United States Patent [19]

Rassman

[11] Patent Number: 5,782,851
[45] Date of Patent: Jul. 21, 1998

[54] HAIR TRANSPLANTATION SYSTEM

[76] Inventor: William R. Rassman. 29391 Laro Dr., Agoura. Calif. 91310

[21] Appl. No.: 630,244

[22] Filed: Apr. 10, 1996

[51] Int. Cl.$^6$ ............................................. A61B 17/34
[52] U.S. Cl. ..................... 636/167; 606/132; 606/133; 606/185; 606/187; 623/15
[58] Field of Search ......................... 606/132, 133, 606/187, 185; 623/15

[56] References Cited

U.S. PATENT DOCUMENTS

| | | | |
|---|---|---|---|
| 1,061,005 | 5/1913 | Parsegan . | |
| 1,694,246 | 12/1928 | Boyne . | |
| 3,945,117 | 3/1976 | Beaver | 30/287 |
| 4,004,592 | 1/1977 | Yamada . | |
| 4,126,124 | 11/1978 | Miller . | |
| 4,451,254 | 5/1984 | Dinius et al. | 604/62 |
| 5,417,683 | 5/1995 | Shiao | 606/1 |
| 5,439,475 | 8/1995 | Bennett | 606/187 |
| 5,578,054 | 11/1996 | Arnold | 606/185 |
| 5,584,851 | 12/1996 | Banuchi | 606/187 |

FOREIGN PATENT DOCUMENTS

| | | |
|---|---|---|
| 0733330 | 5/1966 | Canada . |
| 9212105 | 4/1994 | France . |
| 9509824 | 4/1995 | France . |
| 9405884 | 11/1995 | France . |
| 2231806 | 2/1973 | Germany . |
| 1780736 | 12/1992 | U.S.S.R. . |
| 94/07433 | 4/1994 | WIPO . |

OTHER PUBLICATIONS

Dominic A. Brandy, et al., Utilization of No–Kor Needles for Slit–Micrografting. J. Dermatol. Surg. Oncol., No. 20, 1995, pp. 336–339.

James Arnold. "Pursuing the Perfect Strip: Harvesting Donor Strips with Minimal Hair Transection", International Journal of Aesthetic and Restorative Surgery, vol. 3, No. 2, 1995, pp. 148–153.

Robert M. Bernstein, et al., "Follicular Transplantation", International Journal of Aesthetic and Restorative Surgery, vol. 3, No. 2, 1995, pp. 119–132.

William R. Rassman, et al., "The Art and Science of Minigrafting", Reprint from International Journal of Aesthetic and Restorative Surgery, vol. 1, No. 1, 1993, pp. 27–36.

William R. Rassman, et al., "Micrografting in Extensive Quantities", Reprint from Dermatolgic Surgery, vol. 21, No. 4, Apr. 19, 1995, pp. 306–311.

(List continued on next page.)

*Primary Examiner*—Michael Buiz
*Assistant Examiner*—Daphna Shai
*Attorney, Agent, or Firm*—Fitzpatrick, Cella, Harper & Scinto

[57] ABSTRACT

A system for transplanting hair grafts from a donor region of a patient's scalp to a recipient region of the patient's scalp. The system includes harvesting N (N≧1) strips of skin containing living hair follicles from the donor region of the patient's scalp, the N strips of skin being harvested simultaneously, and cutting the N strips of skin into hair grafts, the N strips of skin being cut simultaneously. The system also includes loading the hair grafts sequentially, bottom down, into a removable cartridge connected to an instrument for implanting the hair grafts into the recipient region of the patient's scalp, the hair grafts being loaded so as to create an air seal between the hair grafts and the cartridge, and implanting the hair grafts. The implanting includes implanting the hair grafts into the recipient region of the patient's scalp, one at a time, using the instrument, by (1) feeding a hair graft to a predetermined feed position in the instrument via air suction created by an air seal between the hair graft and the cartridge, (2) making an incision at a point in the recipient region of the patient's scalp at which the hair graft is to be implanted using a cutting device on the instrument, and (3) sliding the hair graft into the incision using an implanting member in the instrument.

16 Claims, 19 Drawing Sheets

OTHER PUBLICATIONS

William R. Rassman, "Megasessions: Dense Packing", Hair Transplant Forum International, vol. 4, No. 3, May–Jun. 1994.

Richard C. Shiell, "An Australian View of the Las Vegas Meeting", Hair Transplant Forum International, vol. 5, No. 5, Sep.–Oct. 1995.

Michael Beehner, "1995 Las Vegas ISHRS Meeting", Hair Transplant Forum International, vol. 5, No. 5, Sep.–Oct. 1995.

William R. Rassman, "One of our greatest problems . . . Lowballing!", Hair Transplant Forum International, vol. 2, No. 6, Jul.–Aug. 1992.

William R. Rassman,"Concern About Quality", Hair Transplant Forum International, vol. 4, No. 4, Jul.–Aug. 1994.

Michael D. Sparkuhl, "Hair Transplant Surgery The Next Generation", Hair Transplant Forum International, vol. 4, No. 4, Jul.–Aug. 1994.

William R. Rassman, "Trouble With Megasessions and Dense Packing", Hair Transplant Forum, vol. 5, No. 6, Nov.–Dec. 1995.

New Hair Newsletter, vol. 1, No. 3, New Hair Institute, Fall/Winter 1995.

Robert M. Bernstein, "Hair Restoration: Answered Questions.", Reprint from Dermatologic Surgery, vol. 22, 1996, pp. 97–98.

O'Tar T. Norwood, "Gearing Up for Two Thousand Grafts Per Session and Dense Packing", Hair Transplant Forum International, vol. 4, No. 4, Jul.–Aug. 1994.

William R. Rassman, "The Minigraft Revolution: Can We Keep Up Ethically?", Reprint from The American Journal of Cosmetic Surgery, vol. 11, No. 2, 1994, pp. 103–104.

New Hair Institute Update, from Spring 1995 Newsletter, New Hair Institute.

The Fast Track Option: A Common Sense Approach To Hair Transplantation, William R. Rassman, New Hair Institute, ©1994, 1995.

Hair Today And Tomorrow: An Overview Of Old Wives Tales, Wigs, Lotions, Potions, Fact, Fiction And Medical Hair Restoration Options, Marc A. Pomerantz, et al., ©Aug. 1993.

A Buyer's Guide To Hair Transplantation: The Answers Are In The Details, William R. Rassman, New Hair Institute, © 1993.

Videotape entitled "New Hair: The Truth About Transplants", New Hair Institute, © 1994.

New Hair Institute News, vol. 2, No. 1, New Hair Institute, Spring/Summer 1996.

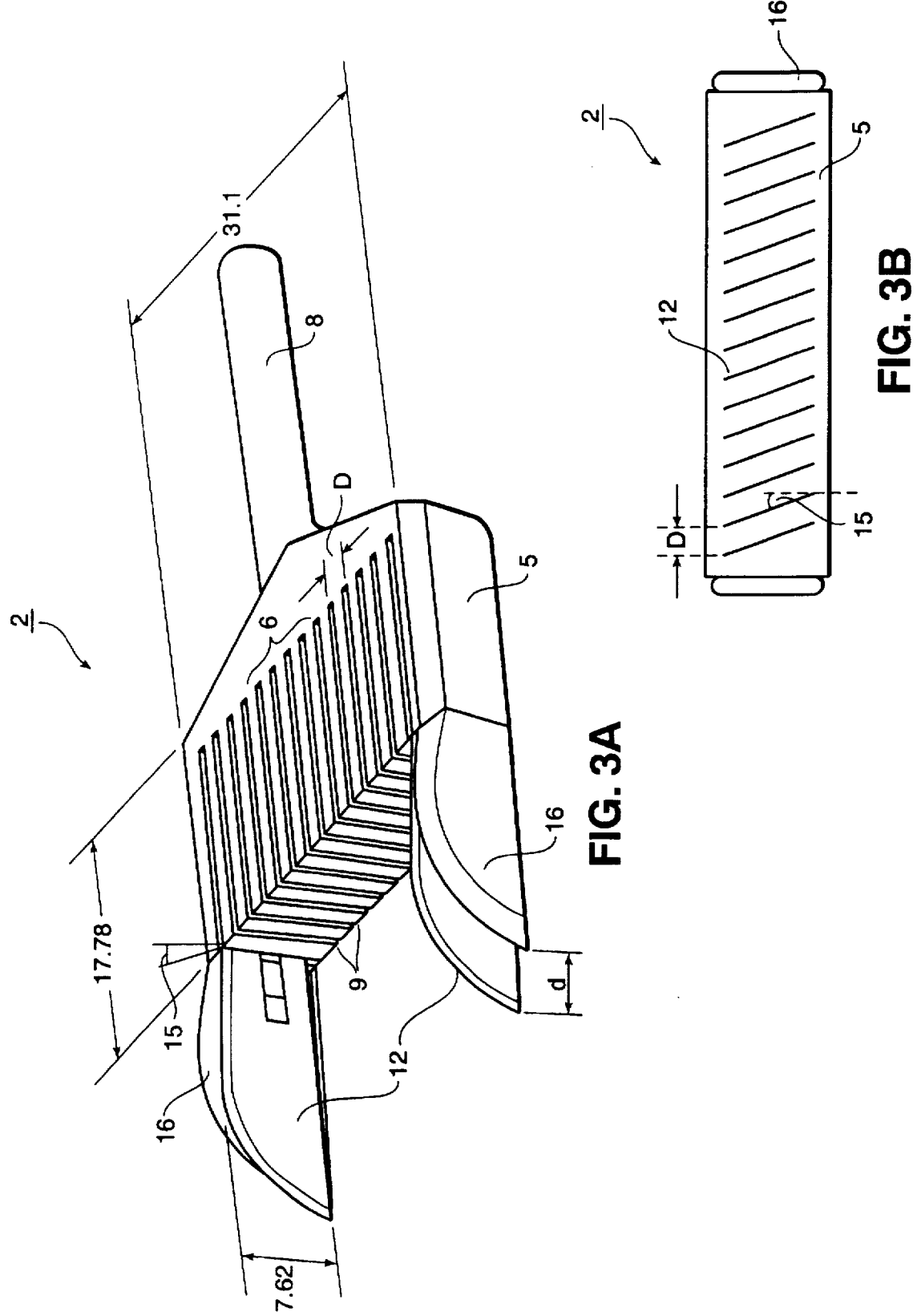

HAIR TRANSPLANTATION SYSTEM

BACKGROUND OF THE INVENTION

1. Field of the Invention

The present invention relates to a hair transplantation system in which a multi-bladed knife harvests strips of skin containing living hair follicles from a donor region of a patient's scalp, a cutting device cuts the strips of skin into very small hair follicle grafts, a cartridge stores the grafts, and an instrument implants grafts fed from the cartridge into a recipient region of the patient's scalp.

2. Description of the Related Art

As is generally known, hair transplantation procedures involve removing hair grafts from a region of a patient's scalp which contains permanently-growing hair, and implanting those hair grafts into a balding region of the patient's scalp.

Traditional hair transplantation procedures, however, often produced undesirable results. For example, as described in Applicant's co-pending U.S. patent application No. 08/444,923, entitled "Hair Implantation Device", the contents of which are hereby incorporated by reference into the subject application, traditional hair transplants often produce a "corn row" appearance. Such an effect generally results from transplanting large hair grafts, of roughly 5 to 25 hairs each, as is commonly done in traditional hair transplantation procedures.

New concepts of hair transplantation are based upon the observation that, in general, hair does not grow singly, but emerges from the scalp in small anatomic units called follicular units. Recently, a hair transplantation procedure called follicular transplantation has been developed which takes advantage of these natural hair groupings. This procedure produces results that are virtually undetectable. That is, it is difficult to distinguish hair grown from a follicular transplant from one's own non-transplanted hair.

In a typical follicular transplant, grafts of 1 to 4 hair follicles per graft, i.e., one follicular unit, are harvested from a donor region of a patient's scalp which contains permanently growing hair. In men, this region, known as the Hippocratic wreath, includes the back and sides of the scalp. Thereafter, the harvested grafts are implanted in balding areas of the patient's scalp. Because very small hair grafts are transplanted in their natural groupings, follicular transplants can produce a head of hair which appears to be to totally natural to the naked eye.

However, because follicular transplant procedures use such small hair grafts, the time it takes to perform such procedures is greatly increased over that of its traditional counterpart, particularly in cases where many grafts (e.g., thousands of grafts) are transplanted. As a result, conventional follicular transplant procedures often may not be completed in just one session.

The large megasession, as defined by the present Applicant, is a large-scale follicular transplant procedure which provides patients with a faster alternative to conventional transplant procedures. In the large megasession, as many as 12 to 16 people at a time work on a single patient. As a result, large numbers of hair grafts, e.g., 3500 or more hair grafts, can be transplanted in a single session. However, even with a large staff, the large megasession can still take over 8 hours.

Using conventional manual techniques, it is not possible to increase the speed of performing transplant procedures without sacrificing the quality of the result and the safety of both the patient and those performing the procedure.

Thus, there exists a need to lessen the amount of time it takes to perform large-scale follicular hair transplants, such as the large megasession, without sacrificing safety and quality.

SUMMARY OF THE INVENTION

The present invention addresses the foregoing need by providing a system of transplanting hair from a donor region of a patient's scalp to a recipient region of the patient's scalp. As described below, the system, which includes both a method and apparatuses used to perform the method, increases both the speed and efficiency at which follicular hair transplants, such as the large megasession, can be performed, without significantly increasing safety risks or reducing hair transplant quality.

According to one aspect, the present invention is a method of transplanting hair grafts from a donor region of a patient's scalp to a recipient region of the patient's scalp. The method includes the steps of simultaneously harvesting N ($N \geq 1$) strips of skin containing living hair follicles from the donor region of the patient's scalp, and simultaneously cutting the N strips of skin into hair grafts. Also included in the method are steps of loading the hair grafts sequentially, bottom down, i.e., subcutaneous layer down, into a removable cartridge connected to an instrument for implanting the hair grafts into the recipient region of the patient's scalp, the hair grafts being loaded so as to create an air seal between the hair grafts and the cartridge, and implanting the hair grafts. The implanting step includes implanting the hair grafts into the recipient region of the patient's scalp, one at a time, using the instrument, by (1) feeding a hair graft to a predetermined feed position in the instrument via air suction created by an air seal between the hair graft and the cartridge, (2) making an incision at a point in the recipient region of the patient's scalp at which the hair graft is to be implanted using a cutting device, such as a blade or a knife, on the instrument, and (3) sliding the hair graft into the incision using an implanting member in the instrument.

The foregoing method has several advantages. For example, by simultaneously harvesting and simultaneously cutting the plural skin strips, the foregoing method makes it possible to reduce hair graft preparation time. As a result, the foregoing hair transplantation method is less time consuming than its conventional counterparts.

In addition, by feeding hair grafts from a cartridge which can be removed and replaced, rather than directly into the instrument itself, the foregoing method decreases both the number of operators needed to load the hair grafts and the time it takes to re-supply hair grafts to the instrument. As a result, both the amount of labor required to perform the hair transplant and overall hair transplantation time are further reduced.

Still further, by using air suction to feed the hair grafts from the cartridge to the instrument, the foregoing method reduces the amount of physical manipulation of the hair grafts during hair graft implantation. As a result, the method reduces the chances that implanted hair grafts will be damaged from manipulation and drying, or contaminated by excessive physical manipulation and/or contact.

According to another aspect, the present invention is a surgical knife which is used in a hair transplantation method to harvest strips of skin containing living hair follicles from a patient's scalp. The surgical knife includes a slotted socket containing plural sockets disposed apart from each other by a predetermined distance, and plural blades. The plural blades are disposed in parallel and at a predetermined angle.

Each of the plural blades has a cutting edge and is disposed in one of the plural sockets on the slotted socket. Also included in the surgical knife are N (N≧1) stops, attached to the slotted socket, each having a thickness greater than that of each of the plural blades, and having a dull edge. The N stops are set back from the cutting edges of the plural blades to prevent the plural blades from cutting into the patient's scalp to greater than a predetermined depth.

Because the foregoing stops prevent the plural blades from cutting into the patient's scalp to greater than a predetermined depth, transplantation errors resulting from improperly-cut strips of skin can be reduced. Along the same lines, injuries to the patient caused by overly-deep incisions can also be reduced.

In preferred embodiments of the surgical knife, the stops comprise a single retainer which slidably fits over the slotted socket, and which holds the plural blades in the slotted socket. In such embodiments, the retainer is manually settable so as to permit a surgeon to control a depth to which the plural blades cut. By virtue of this feature, the surgeon can accurately cut strips of skin from patients having different scalp thicknesses.

According to another embodiment, the present invention is a cutting device for cutting a strip of skin containing living hair follicles which have been harvested from a patient's scalp into hair grafts. The cutting device includes plural blades arranged to be substantially parallel, onto which the strip of skin is placeable. The strip of skin is placeable on the plural blades such that hairs growing from the strip of skin are substantially parallel to the plural blades. Also included in the cutting device are a cutting surface, onto which the plural blades are clamped, and a plate, which is fixed to the cutting surface and which is movable to contact the plural blades upon application of a force. The plate has sufficient mobility to contact the plural blades with enough force to cause the plural blades to cut the strip of skin into the hair grafts. A rake having plural prongs fits between the plural blades.

Because the foregoing cutting device includes plural blades, onto which one or more strip(s) of skin can be placed, the cutting device is able to produce a large number of hair grafts at a single time. As a result, the cutting device is able to increase the speed at which a hair transplantation procedure is performed. In addition, because the plural blades are arranged to be substantially parallel, the foregoing cutting device increases the uniformity of hair grafts cut thereby.

In preferred embodiments of the cutting device, the plural prongs on the rake comprise plural hooks which grab onto a strip of hair. In such embodiments, a second strip of skin is placeable on the blades, top down, i.e., skin exterior down, such that hairs growing from the second strip of skin extend downward between the plural blades and are substantially parallel to the plural blades. Each of the hooks on the rake grabs onto the second strip of skin so that the rake can be used to pull the second strip of skin through the blades.

By pulling the strip of skin through the blades, the second strip of skin can be cut into plural narrow strips of skin. This means of cutting plural narrow strips of skin from a single strip of skin reduces injuries to hair follicles caused by conventional, pressure-dependent, cutting mechanisms.

In still other preferred embodiments, each of the plural prongs on the rake fits between two of the plural blades in order to facilitate removal of cut hair grafts from between the plural blades. In such embodiments, preferably, the rake is located beneath the plural blades and is drawn up through the plural blades, thereby lifting out any cut hair grafts from between the plural blades.

According to still another aspect, the present invention is a cartridge for storing plural hair grafts which have been harvested from a patient's scalp, each of the plural hair grafts containing N (N≧1) hair follicles. The cartridge includes a tubular body having a continuous throughbore, the continuous throughbore having a cross-sectional area sufficient to accommodate a single hair graft, and a neck, connected to the tubular body, through which each of the plural hair grafts is sequentially loaded, bottom down, into the tubular body. A slot runs along the neck, for permitting contact with a hair graft in the neck by an external instrument. The external instrument slides the hair graft along the slot to load the hair graft into the cartridge.

In the foregoing cartridge, preferably, the neck has a funnel shape such that a top portion of the neck has a greater radius than a bottom portion the neck which connects to the tubular body.

The foregoing cartridge facilitates storage, handling and maintenance of hair grafts. More specifically, because the hair grafts are fed into the tubular body via a funnel-shaped neck having a greater radius at a top portion than at a bottom portion which connects to the tubular body, injuries to the hair grafts during loading are reduced. That is, by gradually deforming the hair grafts to fit into the tubular body using the funnel-shaped neck, the foregoing cartridge reduces injuries to the hair grafts, such as edge tears, which can be caused by attempting to force large grafts into narrow storage areas.

In preferred embodiments of the cartridge, the continuous throughbore has a cross-sectional area which is less than a cross-sectional area of each hair graft loaded into the cartridge. As a result, an air seal is created between each hair graft and the tubular body of the cartridge. This air seal creates a suction when a hair graft is fed out from the cartridge, which pulls the next-sequential hair graft from the cartridge. Thus, the foregoing cartridge reduces physical contact to the hair grafts during feeding of the hair grafts to the instrument.

Still further preferred embodiments of the invention include a pressurizing mechanism, attached to a top of the cartridge, for pressurizing hair grafts within the cartridge. Pressure applied from the pressurizing mechanism aids movement of the hair grafts down the tubular body of the cartridge, and reduces the chances that hair grafts will get stuck in the cartridge during feeding.

According to still another aspect, the present invention is an instrument for implanting hair grafts into a patient's scalp, which, through action of air suction in an air-sealed cartridge containing the hair grafts, are fed, bottom down, to an implantation-ready position as a preceding hair graft is implanted. The instrument includes an elongate housing adapted to be manipulated by a surgeon during implantation of the hair grafts, and a cutting device, such as a blade or a knife, affixed to an end of the elongate housing for making an incision into the patient's scalp, into which a hair graft is to be implanted. Also included in the instrument is a feeding tube which connects the instrument to the cartridge, which stores the hair grafts, and which feeds a hair graft from the cartridge to a predetermined feed position. The feeding tube includes a vent positioned at the predetermined feed position, such that when the hair graft is moved to the predetermined feed position, air from the vent breaks an air seal between the hair graft and a next-sequential hair graft in the cartridge. An implanting member (1) moves downward through the elongate housing, (2) contacts the hair graft at the predetermined feed position, and (3) slides the hair graft into the incision made in the patient's scalp by the cutting device through an opening formed between the cutting device and the elongate housing. A plunger, disposed within the elongate housing, actuates the implanting member.

By virtue of the foregoing configuration, the instrument is able to feed hair grafts from a connected cartridge by means of air suction. As a result, the amount of physical contact to each hair graft during implantation is reduced, thereby reducing both the chances of injuries to, and contamination of, the hair grafts.

Preferred embodiments of the instrument also include a holding member. In these embodiments, the holding member (1) moves downward through the elongate housing in a substantially same direction as the implanting member, (2) contacts the hair graft contacted by the implanting member, and (3) remains in contact with the hair graft during withdrawal of a portion of the instrument from the incision. In addition, the plunger, preferably, is also used to actuate the holding member.

Advantageously, the foregoing holding member, by remaining in contact with an implanted hair graft during withdrawal of the portion of the instrument, reduces the chances that the implanted hair graft will be dislodged during withdrawal of the portion of the instrument.

Preferably, the implanting member and the holding member move independently, such that the holding member remains in contact with an implanted hair graft while the implanting member is being withdrawn from the incision. This feature reduces the chances that a newly-implanted hair graft will be dislodged during withdrawal of the implanting member. In such embodiments, a latch or the like can be used to trigger withdrawal of the implanting member from the incision, whereas the holding member is withdrawn from the incision when pressure is removed from the plunger.

In embodiments of the instrument that do not include a holding member, the foregoing function can be achieved by withdrawing the implanting member while a portion of the instrument remains in the incision to hold an implanted hair graft in place.

In further preferred embodiments of the foregoing instrument, the holding member extends outside of the elongate housing when holding a hair graft in an incision. In such embodiments, the holding member includes an expandable tip at an area which contacts the hair graft, which expands when the holding member is outside of the elongate housing. Preferably, the expandable tip is made of a sponge-type material, and has a size which is sufficient to permit the expandable tip to surround the implanting member while the implanting member is being withdrawn from the incision.

By virtue of the expandable tip, the foregoing instrument is able to reduce injuries to implanted hair grafts caused during withdrawal of the implanting member, and caused by excessive pressure applied to the holding member.

In still further preferred embodiments of the foregoing instrument, the cutting device, e.g., the blade or knife, has a substantially smooth planar surface so as to reduce injuries to hair grafts during implantation which result from friction between the hair grafts and the planar surface, or from protrusions found on the planar surface.

In still further preferred embodiments, a stop, such as a mechanical resistor or the like, is placed at the predetermined feed position, so as to reduce the chances that a hair graft will be fed or ejected from the feeding tube prematurely.

This brief summary has been provided so as that the nature of the invention may be understood quickly. A more complete understanding of the invention can be obtained by reference to the following detailed description of the preferred embodiments thereof in connection with the attached drawings.

BRIEF DESCRIPTION OF THE DRAWINGS

FIGS. 3A and 3B show perspective views of a surgical knife of the present invention.

DETAILED DESCRIPTION OF THE PREFERRED EMBODIMENTS

The present invention is a system for transplanting hair grafts from a donor region of a patient's scalp to a recipient region of the patient's scalp. The system of the present invention includes simultaneously harvesting N (N≥1) strips of skin containing living hair follicles from the donor region of the patient's scalp, and simultaneously cutting the N strips of skin into hair grafts. Also included in the system are steps of loading the hair grafts sequentially, subcutaneous layer-down, i.e., bottom down, into a removable cartridge connected to an instrument for implanting the hair grafts into the recipient region of the patient's scalp, the hair grafts being loaded so as to create an air seal between the hair grafts and the cartridge, and implanting the hair grafts. The implanting step includes implanting the hair grafts into the recipient region of the patient's scalp, one at a time, using the instrument, by (1) feeding a hair graft to a predetermined feed position in the instrument via air suction created by an air seal between the hair graft and the cartridge, (2) making an incision at a point in the recipient region of the patient's scalp at which the hair graft is to be implanted using a cutting device on the instrument, and (3) sliding the hair graft into the incision using an implanting member in the instrument.

Figure 1:
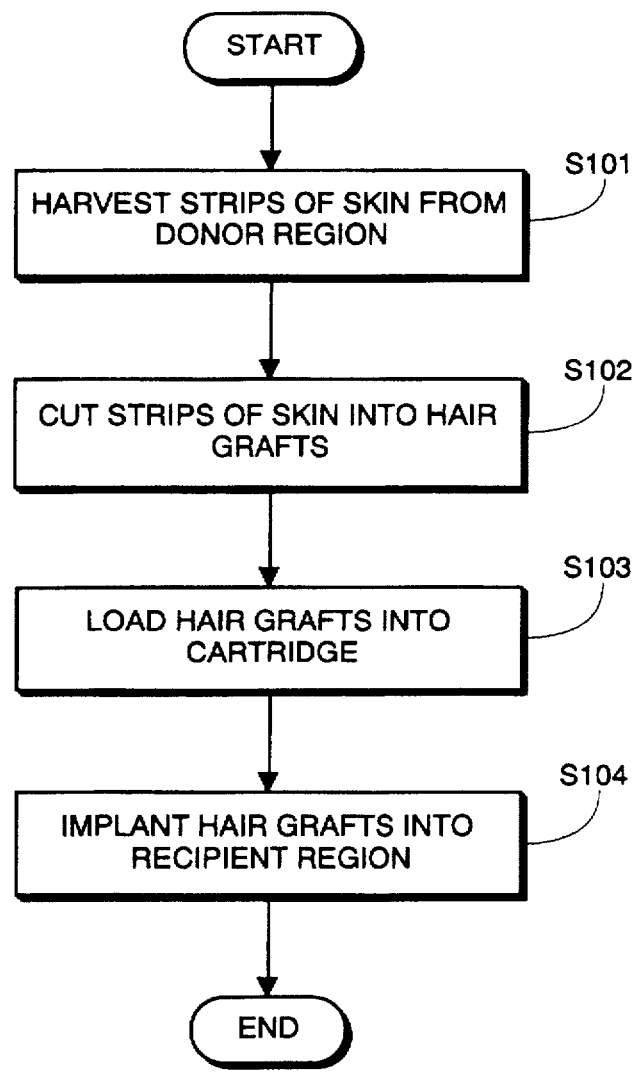
FIG. 1 is a flow diagram showing a hair transplantation procedure of the present invention.

The foregoing system is depicted as process steps in FIG. 1. As described in more detail below, each of these process steps is performed using a different device. Accordingly, the following provides a description of both the process steps shown in FIG. 1, and of the devices used to perform those process steps.

Figure 2:
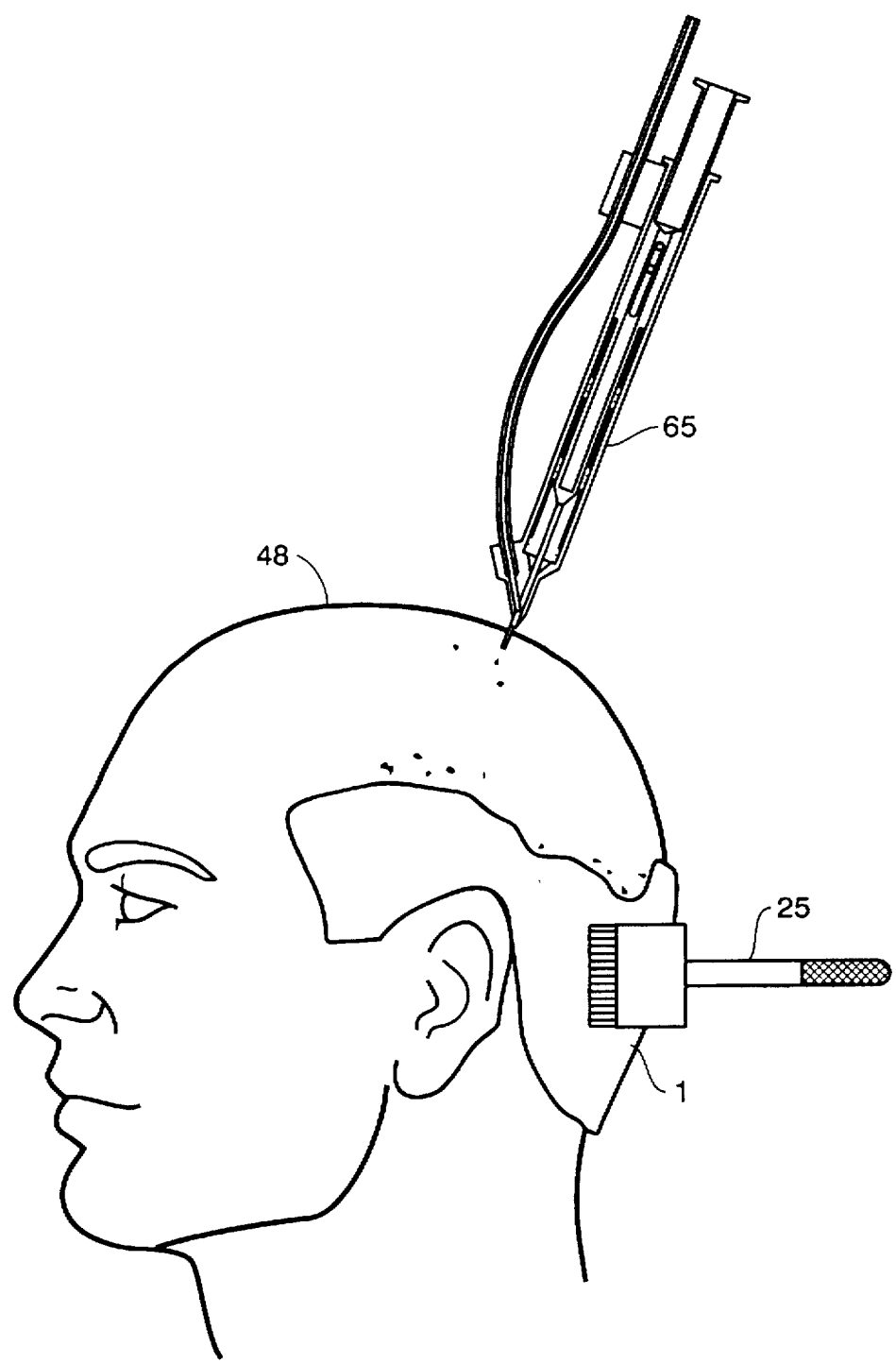
FIG. 2 shows a profile view of a patient undergoing the hair transplantation procedure of the present invention.

In step S101, one or more strip(s) of skin containing living hair follicles are harvested from a donor region of the patient's scalp. The donor region comprises a region of the patient's scalp which contains permanently growing hair. As shown in FIG. 2, donor region 1 for a man typically comprises the Hippocratic wreath.

In step S101, either one or more wide strips of skin is harvested, or plural narrow strips of skin are harvested. Typically, the narrow strips of skin have widths which are approximately equal to the width of a single hair graft, whereas the wide strips of skin have widths which are greater than that of a single hair graft. Harvesting of wide strips of skin from the patient's head is done using conventional surgical techniques. Accordingly, a detailed description of this process is omitted for the sake of brevity.

Harvesting of plural narrow strips of skin from the patient's head is done using the surgical knife of the present invention described below.

Surgical Knife

Figure 4A:
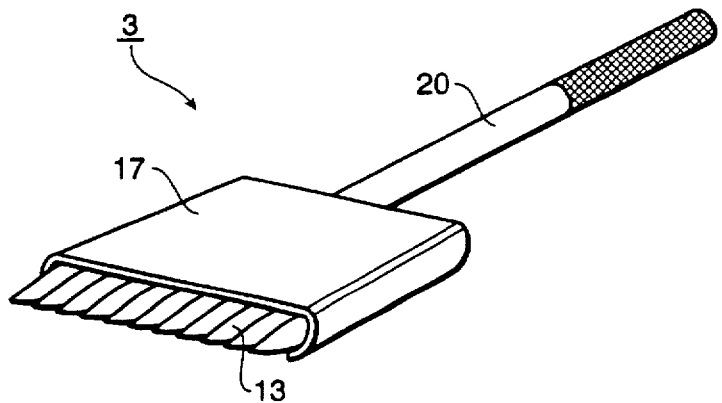
FIGS. 4A, 4B and 4C show perspective views of a surgical knife of the present invention having a single retainer stop.
Figure 4B:
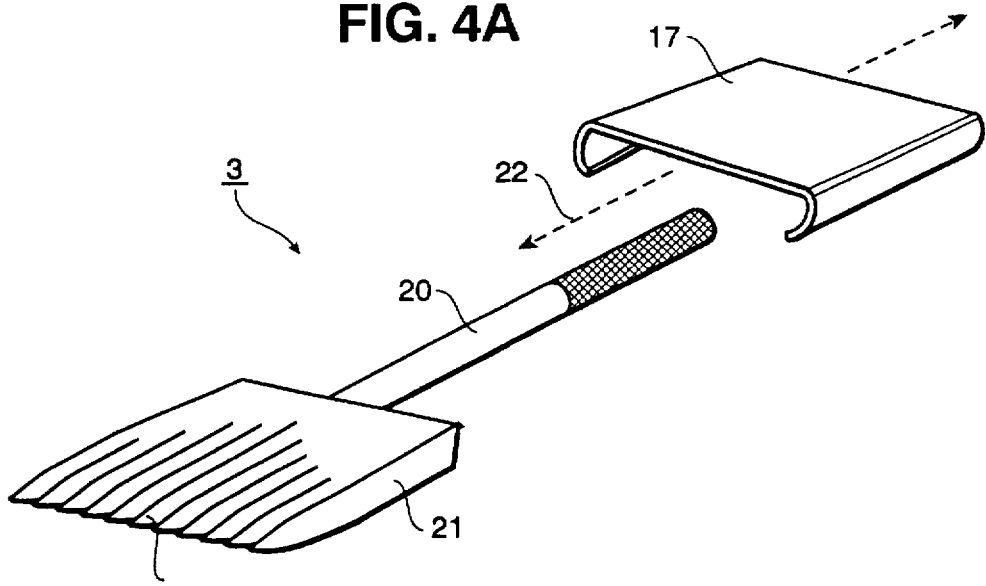
Figure 4C:
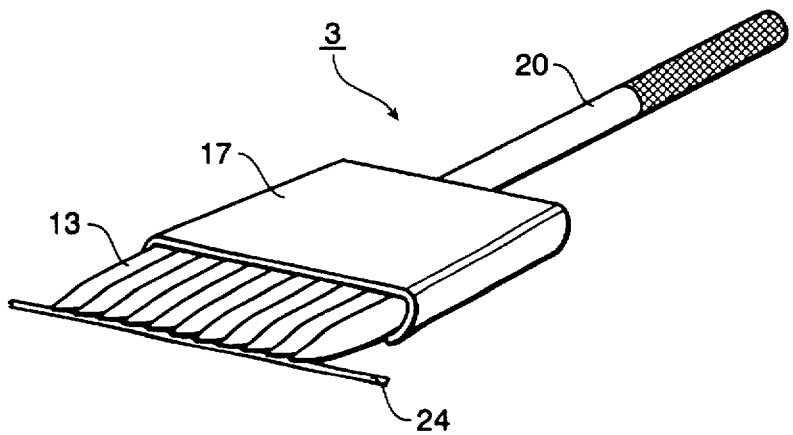

A first representative embodiment of the surgical knife of the invention is shown in FIGS. 3A and 3B, and a second representative embodiment of the surgical knife of the present invention is shown in FIGS. 4A to 4C. Each of these embodiments includes a slotted socket containing plural slots disposed apart from each other by a predetermined distance, and plural blades, each having a cutting edge, and each being disposed in one of the plural slots on the slotted socket. The plural blades are disposed in parallel and at a predetermined angle. N (N≧1) stops are attached to the slotted socket. Each stop has a thickness greater than that of each of the plural blades, and has a dull edge. These stops are set back from the cutting edges of the plural blades to prevent the plural blades from cutting into the patient's scalp to greater than a predetermined depth.

FIGS. 3A and 3B show perspective and face-on views, respectively, of surgical knife 2, which is a surgical knife according to the present invention. As shown in FIGS. 3A and 3B, surgical knife 2 includes slotted socket 5 containing plural female slots 6, and handle 8 by which a surgeon manipulates surgical knife 2. Slots 6 are spaced apart from each other by a predetermined distance, labelled D in FIGS. 3A and 3B. This predetermined distance is defined by fingers 9, shown in FIG. 3A. To use surgical knife 2 to harvest micrograft-sized strips of skin, i.e., strips of skin having a width approximately equal to that of a single micrograft-sized hair graft, each of fingers 9 should have a width between 1 and 3 millimeters. However, the width of each of fingers 9 can vary, depending upon the size of the grafts to be cut from the strips of skin.

Surgical knife 2 includes plural blades 12, as shown in FIGS. 3A and 3B (see also reference numeral 13 in the second embodiment shown in FIGS. 4A to 4C). Each of blades 12 fits into a corresponding one of slots 6. It is noted that surgical knife 2 shown in FIG. 3A shows only two blades. This is done for simplicity of view and for discussion purposes only. In actuality, surgical knife 2, like surgical knife 3 shown in FIGS. 4A to 4C, includes a blade in each of slots 6, as shown in FIG. 3B. In this regard, each slot in slotted socket 5 should have a width which is sufficient to accommodate a base of a blade, and to hold the blade in place even when a force is applied to the blade. Moreover, surgical knife 2 can be fashioned to accommodate any number of blades, as desired by a user.

As shown in FIGS. 3A and 3B, blades 12 are substantially parallel and are aligned in slotted socket 5 so as to cut to substantially the same depth. In addition, each blade in slotted socket 5 is angled around the cutting axis at predetermined angle 15. In preferred embodiments of the surgical knife, this angle is between 15° and 45°, with the most preferred angle being 30°. Such angles reduce damage to subcutaneous follicles since hair rarely grows perpendicularly from the scalp but rather grows at an inclined angle. By angling the cutting blades around the cutting axis, it is possible to facilitate cutting at the same angle as the hair grows and thereby to minimize damage to follicles.

The foregoing angular arrangement of blades 12 also facilitates cutting of the strips of skin. That is, since blades 12 tend to cut through areas of skin which provide the least resistance, hair follicles, which provide greater resistance than surrounding skin, will be pushed aside during cutting by angled blades, such as blades 12.

Attached to slotted socket 5 are one or more stops, such as stops 16, shown in FIGS. 3A and 3B, and stop 17, shown in FIGS. 4A to 4C. Stops typically have dull edges, which can be squared or rounded. As shown, stops are used in the surgical knife in order to provide cutting depth control. That is, stops 16, for example, are positioned so as to prevent blades 12 from cutting to greater than a predetermined depth into a patient's scalp. This predetermined depth is defined by the distance "d", shown in FIGS. 3A and 3B, that the blades extend beyond the stops.

FIGS. 3A, 3B and 4A to 4C show examples of different types of stops. FIGS. 3A and 3B show stops 16, which are formed as integral parts of slotted socket 5, which are located adjacent to oppositely-positioned blades, and which jut out from slotted socket 5. Stops 16 have a shape similar to that of blades 12, but have dull edges so as to prevent blades 12 from cutting too deeply into the patient's scalp. Stops of this type are preferably also thicker than blades 12, in order to guard against penetration of the scalp.

FIGS. 4A to 4C, on the other hand, show stop 17, which also functions as a retainer for blades 13 in slotted socket 21. That is, as shown in FIGS. 4A and 4B, stop 17 slides overtop both handle 20 and slotted socket 21 of surgical knife 3 in the direction of arrow 22. In this manner, stop 17 is both able to prevent blades 13 from cutting too deeply into a patient's scalp, and to aid in the retention of blades 13 in slotted socket 21.

In this regard, stop 17 can also be used to insert and to align blades 13 in slotted socket 21. That is, when inserting blades 13 into the slots in slotted socket 21, it helps to push those blades against a flat surface, such as a table, to attain proper alignment. When blades 13 are pushed too hard, they may dislodge from slotted socket 21. However, in surgical knife 3, as shown in FIG. 4C, when stop 17 is slid forward, blades 13 can be pressed against flat surface 24 at a greater force than would otherwise be possible, since stop 17 acts to retain the blades in their respective slots.

Moreover, because stop 17 slidably fits over slotted socket 21, stop 17 can be manually adjusted to accommodate different scalp thicknesses. Thus, if a patient has an unusually thick scalp, a surgeon need merely slide stop 17 away from the blades in order to provide for a deeper cut, or vice versa, as the case may be. In addition, because stop 17 can slide on and off of slotted socket 21, as shown by arrow 22 of FIG. 4B, damaged or worn blades within slotted socket 21 can be easily replaced.

At this point, it is noted that a single surgical knife according to the present invention can include both stops 16 and 17.

In preferred embodiments, slotted sockets 5 and 21 are made from an extrusion plastic mold, thus reducing the amount of time, effort and cost required for manufacture. Thus, these slotted sockets can be easily disposed of and replaced at little cost. It is noted, however, that slotted sockets 5 and 21 can also be made from stainless steel or other metals, as desired.

Preferred dimensions of a surgical knife according to the present invention are shown in FIG. 3A in millimeters. It is, however, noted, that the dimensions of the present surgical knife can be varied to accommodate a surgeon's needs.

FIG. 2 shows surgical knife 25, which can be either a surgical knife of the first embodiment or of the second embodiment, being used to harvest strips of skin from donor region 1 of a patient's scalp during a hair transplantation procedure. Surgical knife 25 cuts strips of skin containing living hair follicles from donor region 1 by pressing against the patient's scalp, and cutting.

Figure 5A:
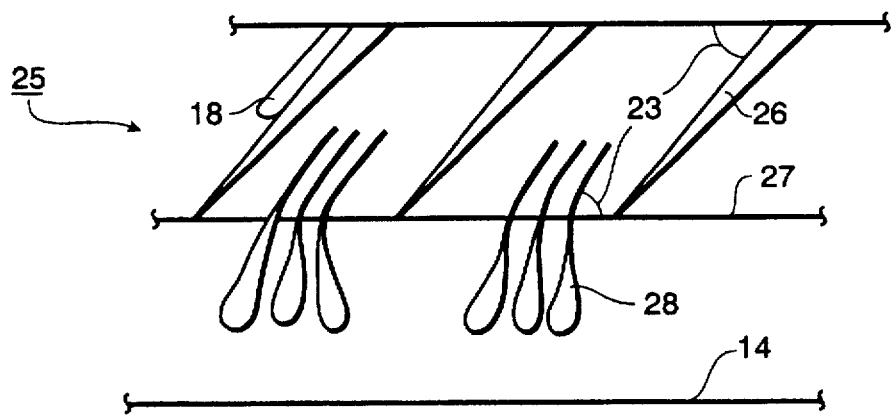
FIGS. 5A, 5B and 5C show the surgical knife of the present invention being used to cut strips of skin.
Figure 5B:
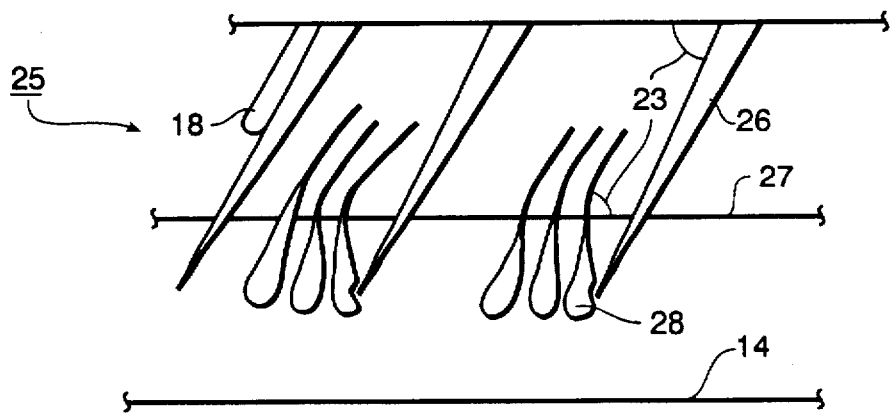
Figure 5C:
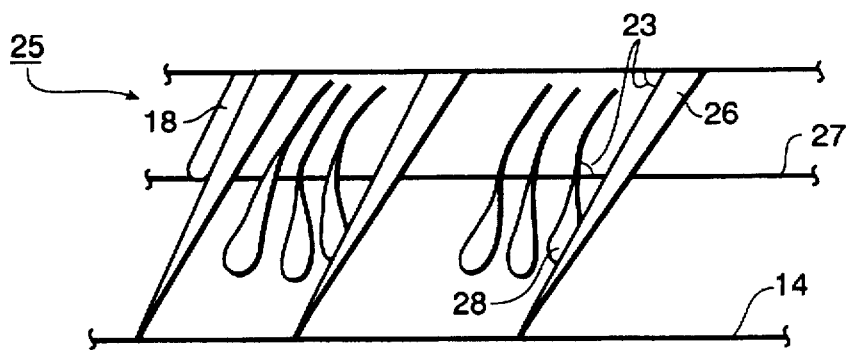

FIGS. 5A to 5C show a close-up view of surgical knife 25 being used to cut plural strips of skin from a scalp. More specifically, FIG. 5A shows blades 26 of surgical knife 25 approaching scalp 27 containing hair follicles 28 grouped in a follicular unit. FIG. 5B shows blades 26 cutting through scalp 27. As shown in FIG. 5B, because blades 26 are angled at substantially the same angle that hairs grow out of scalp 27 (see angles 23), blades 26 follow the path of least resistance when cutting and push hair follicles 28 aside, rather than cutting through hair follicles 28. This phenomenon is further shown in FIG. 5C, which shows blades 26 cutting all the way through to skull 14 without significantly damaging hair follicles 28. As also shown in FIG. 5C, stop 18 prevents surgical knife 25 from cutting into skull 14.

Referring back to FIG. 1, once strips of skin containing living hair follicles have been harvested from the patient's scalp in step S101, the process proceeds to step S102.

In step S102, strips of skin containing living hair follicles are cut into individual hair grafts. In the present hair transplantation system, micrografts are preferred; however, it is noted that any size graft can be cut. Examples of different hair grafts which can be cut are standard grafts, containing more than 12 hair follicles per graft; minigrafts, containing 5 to 9 hair follicles per graft; and micrografts containing 1 to 4 hair follicles per graft. Smaller grafts are generally preferred in follicular transplant procedures because they provide a more natural look than do larger grafts, with the most preferred graft size being the follicular unit, defined above.

Step S102 is performed differently for narrow strips of skin than for wide strips of skin. More specifically, wide strips of skin must first be cut into narrow strips of skin, before being cut into individual hair grafts. Narrow strips of skin, on the other hand, can be cut directly into hair grafts. Different processes for cutting hair grafts from strips of skin having different widths are described below.

Furthermore, in step S102, the cutting can be performed either manually or using a specially-designed cutting device. Manual cutting will be described first, followed by cutting using the cutting device.

Manual cutting according in the present invention can be done using standard surgical techniques. More specifically, in a case where wide strips of skin have been harvested, a surgeon must first cut the wide strips of skin into plural narrow strips of skin having a width approximately equal to that of a single hair graft. Thereafter, the surgeon must cut the plural narrow strips of skin into individual hair grafts.

In a case where plural narrow strips of skin have been harvested using the above-described surgical knife, for example, a surgeon need merely cut individual hair grafts from the plural narrow strips of skin. Preferably, the surgeon cuts the plural narrow strips simultaneously in order to save time, however, this is not required.

During manual cutting, care must be taken to cut the strips of skin at an angle so as to reduce damage to hair follicles during cutting. More specifically, as shown in FIGS. 5A to 5C, hair grows at an angle (angle 23) from the scalp. Accordingly, when cutting hair grafts manually from strips of skin, the cutting should be done at the growth angle, which is generally between 0° and 45°, with the most common growth angle being approximately 30°.

In the present invention, manual cutting of the strips of skin is done on a translucent surface so that hairs on the strips of skin can be easily detected. In addition, in the present invention, light filters can cover the translucent surface so as further to facilitate detection of hairs on the strips of skin. Polarized light and external light may also be used to accentuate the visibility of hairs on the strips of skin.

In preferred embodiments of the present invention, the manual cutting surface is cooled and moistened with saline so as to prolong the viability of the strips of skin.

Cutting Device

As an alternative to the often time-consuming and imprecise process of manual cutting, the present invention provides a cutting device to cut strips of skin. The cutting device can be used both to cut wide strips of skin into narrow strips of skin, and to cut narrow strips of skin into hair grafts, as described in more detail below.

The cutting device includes plural blades arranged to be substantially parallel, onto which a strip of skin is placeable. The strip of skin is placeable on the plural blades such that hairs growing from the strip of skin are substantially parallel to the plural blades. Also included in the cutting device is a cutting surface, onto which the plural blades are clamped. A plate is fixed to the cutting surface and is movable to contact the plural blades upon application of a force. The plate has sufficient mobility to contact the plural blades with enough force to cause the plural blades to cut the strip of skin into the hair grafts. A rake, having plural prongs, fits between the plural blades.

Figure 6A:
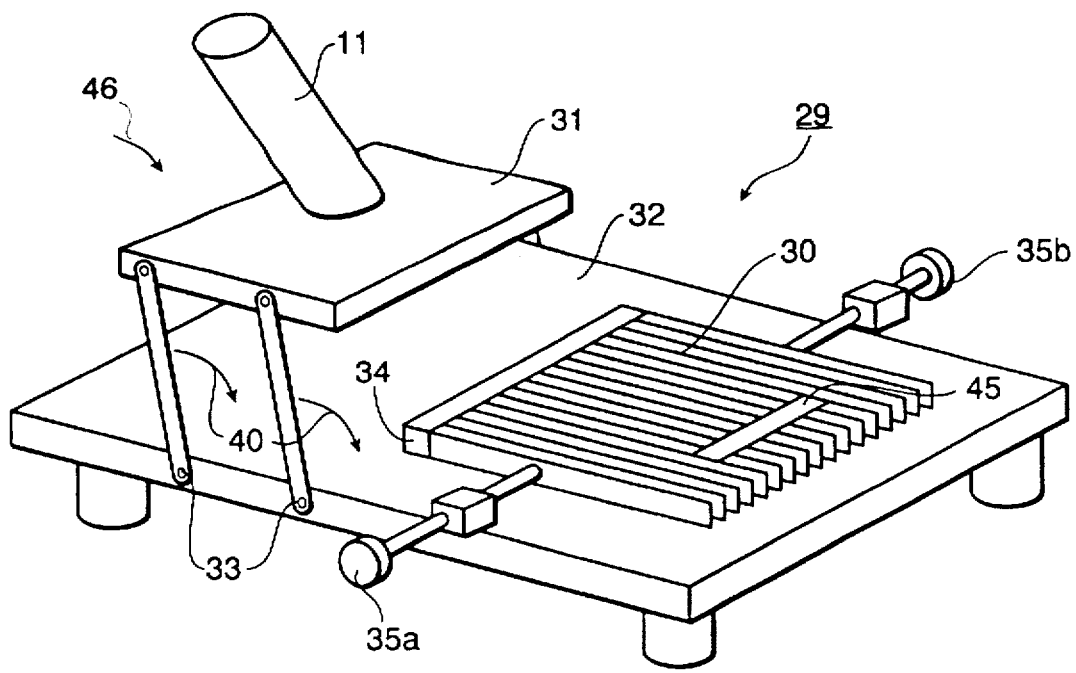
FIGS. 6A, 6B, 6C, 6D, 6E, 6F, 6G and 6H show views of embodiments the cutting device of the present invention.

A representative embodiment of the cutting device of the present invention is shown in FIGS. 6A through 6G. FIG. 6A shows cutting device 29 in an "open" position. As shown, cutting device 29 includes plural blades 30, plate 31, cutting surface 32, rotatable members 33, guide 34, handle 11 and a rake, such as rake 35, shown in FIG. 6C, and/or rake 58, shown in FIG. 6F. Each of these features is described below in detail.

As noted above, cutting device 29 includes plural blades 30. Blades 30 are arranged substantially parallel on cutting surface 32. Blades 30 are also arranged substantially perpendicular to cutting surface 32, i.e., at roughly 90° to cutting surface 32.

As shown in FIG. 6A, each of blades 30 has a substantially same height, such that blades 30 define a plane which is substantially parallel to cutting surface 32. It is noted that the number and sizes of blades used can vary, depending upon a surgeon's requirements, so long as they vary in unison.

Blades 30 are held in position by guide 34. As shown in FIG. 6A, guide 34 is located at one end of blades 30. So as not to interfere with cutting of strips of skin, guide 34 should have a height which is less than or equal to the height of blades 30. It is noted that although the embodiment of the cutting device described herein shows only one guide, any number of guides can be employed.

As also shown in FIG. 6A, blades 30 and guide 34 are clamped to cutting surface 32 via conventional mechanical clamps 35a and 35b. It is noted that although screw-type clamps are shown in FIG. 6A, any clamping mechanism can be used to clamp blades 30 and guide 34 to cutting surface 32.

Cutting device 29 also includes plate 31, which is fixed to cutting surface 32 by connectors, such as rotatable members 33. Plate 31 preferably has a smooth planar surface which is substantially parallel to the plane defined by blades 30. Force is applied to plate 31 by handle 11, also shown in FIGS. 6A and 6B.

Figure 6B:
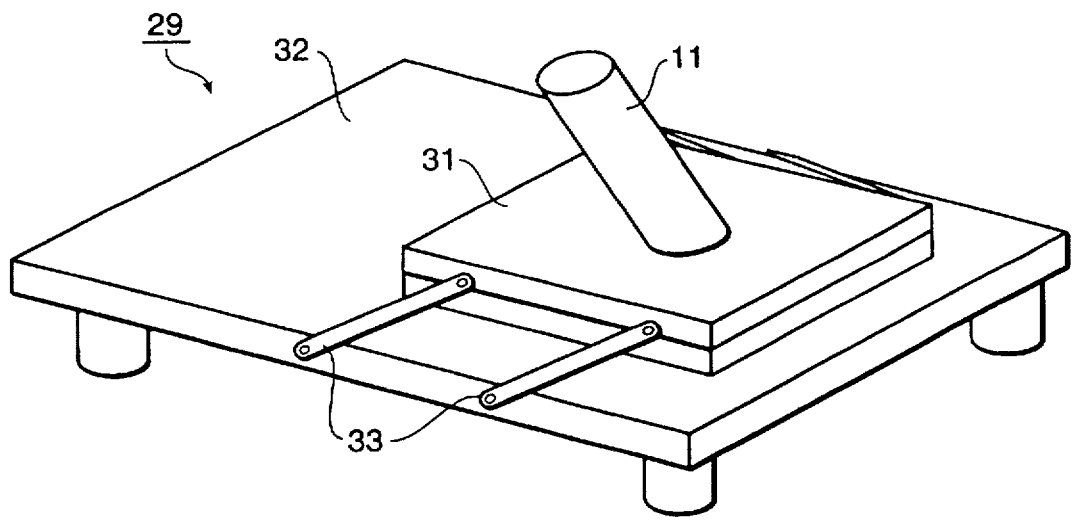

With respect to rotatable members 33, it is noted that while FIG. 6A shows two rotatable members on each side of plate 31, any number N (N ≧ 1) of rotatable members can be used on each side of plate 31. As shown in FIG. 6A, rotatable members 33 rotate in the direction of arrows 40 toward blades 30. Upon application of sufficient force via handle 11, or otherwise, rotatable members 33 move plate 31 into contact with blades 30, as shown in FIG. 6B. Upon removal of that force, in preferred embodiments, rotatable members 33 reset plate 31 to its open position, depicted in FIG. 6A.

It is noted that cutting device 29 is not limited to using rotatable members to move plate 31 into contact with blades 30. Rather, any equivalent mechanism can be used. For example, in another embodiment of the cutting device, shown in FIG. 6H, plate 31 is positioned above blades 30 by a spring mechanism, such as spring mechanism 33a or its substantial equivalent, and is pushed into contact with blades 30 using handle 11a, which compresses spring mechanism 33a to cause plate 31 to contact blades 30. It is noted that hinges can also be used in place of spring mechanism 33a.

Figure 6C:
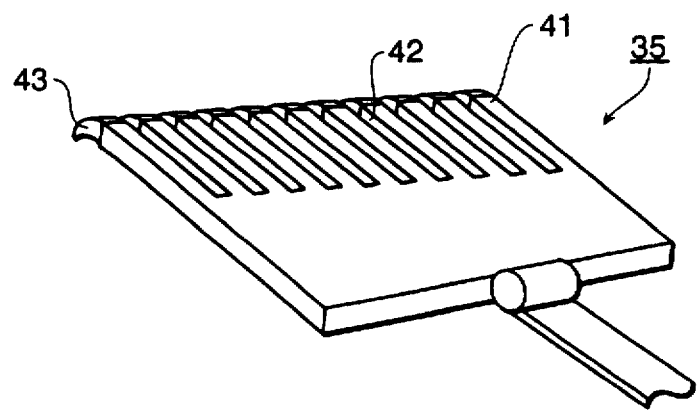
Figure 6D:
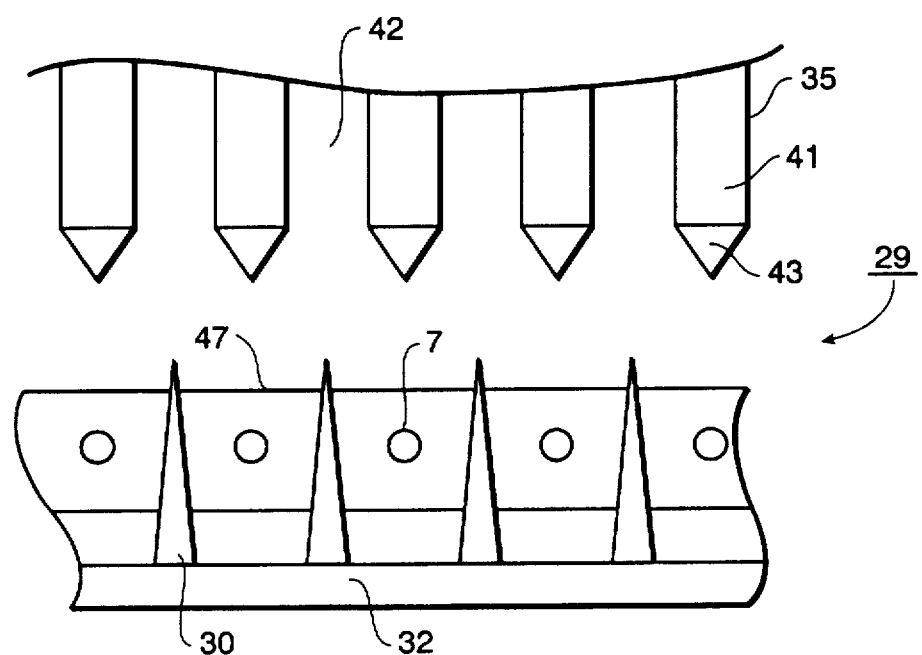
Figure 6E:
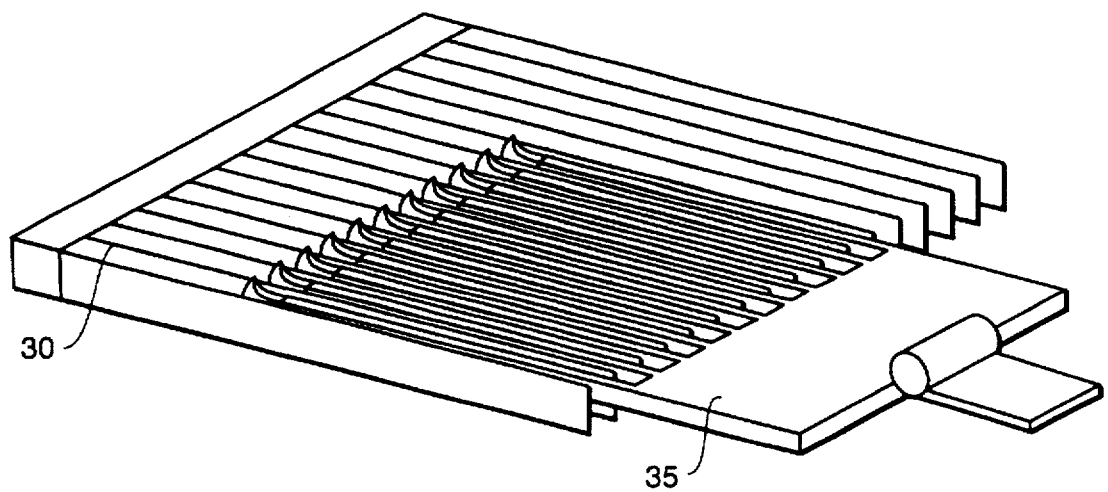

Rake 35, shown in FIG. 6C, is a first embodiment of a rake which can be included within cutting device 29. Rake 35 is comb-shaped and includes plural prongs 41 for removing cut skin from between blades 30, as described below. To this end, in preferred embodiments, prongs 41 are separated by slots 42, each having a thickness sufficient to accommodate one of blades 30. Preferably, rake 35 is removable from cutting device 29, as shown in FIG. 6C. However, rake 35 can also be permanently attached to cutting device 29, so as to reduce the chances of rake 35 being misplaced.

In rake 35, each of prongs 41 includes a tip, such as tip 43, shown in FIG. 6C. In preferred embodiments of the invention, each tip is hook-shaped so that it can grab a strip of skin and hold the strip when being pulled.

Figure 6F:
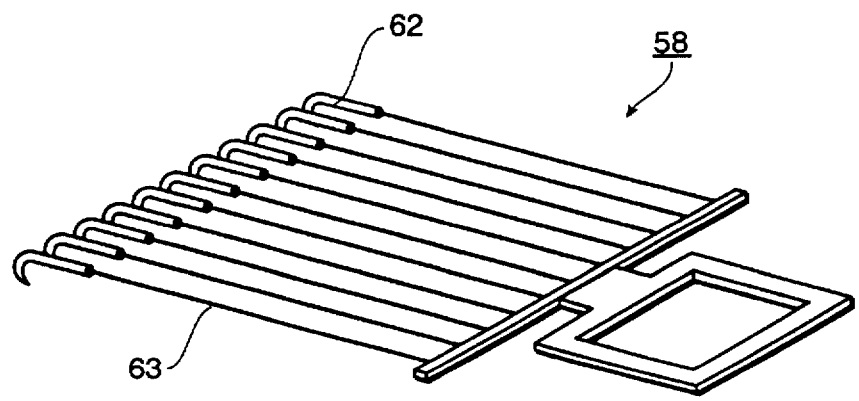
Figure 6G:
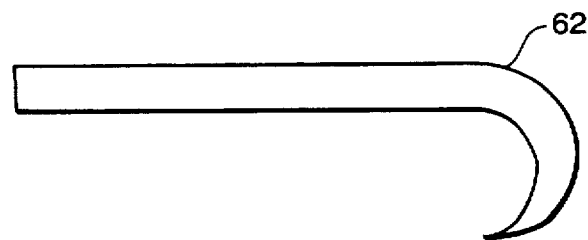
Figure 6H:
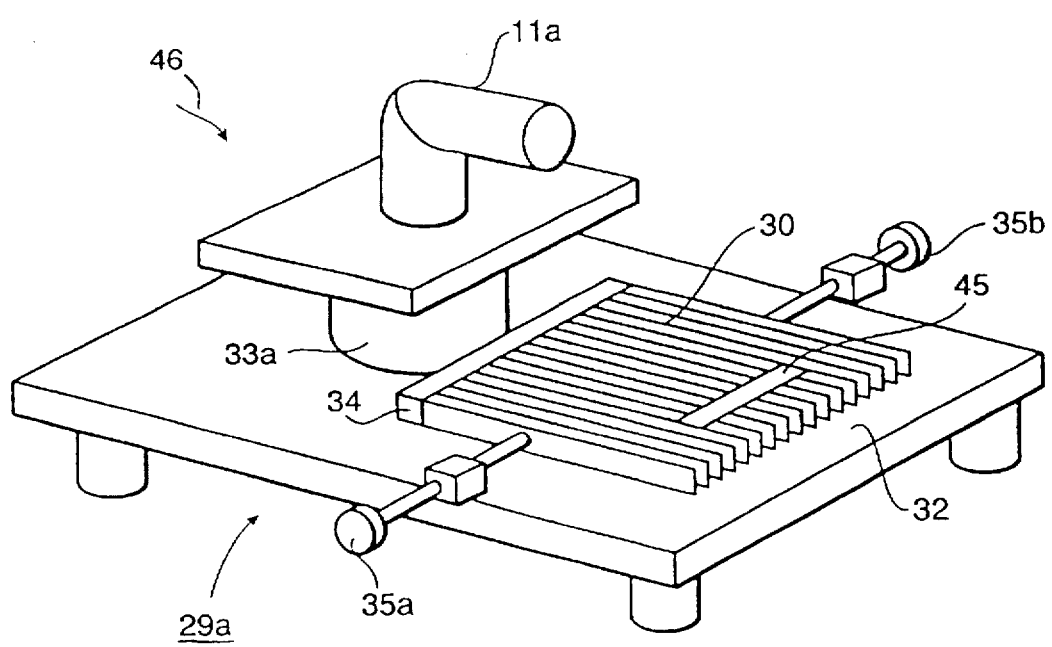

FIG. 6F shows a second embodiment of a rake which can be included with cutting device 29. Rake 58 includes hooks 62, of which a side view is shown in FIG. 6G, which are used to grab a strip of skin and hold the strip while being pulled. In preferred embodiments, each of hooks 62 has a width which is substantially less than the distance between two of plural blades 30. However, it is noted that hooks 62 can be any width.

In a case where each of hooks 62 has a width which is substantially less than the distance between plural blades 30, cutting device 29 may include both rakes 35 and 58, with rake 35 being used primarily to remove hair grafts from between blades 30, and rake 58 being used primarily to grab onto a strip of skin when the strip of skin is pulled. In such cases, prongs 63 on rake 58 can be made of wire in order to facilitate pulling.

Preferably, all components of cutting device 29, including rakes 35 and 58, are made from polished stainless steel which is substantially free from crevices so as to reduce amounts of contaminants on cutting device 29.

Figure 7A:
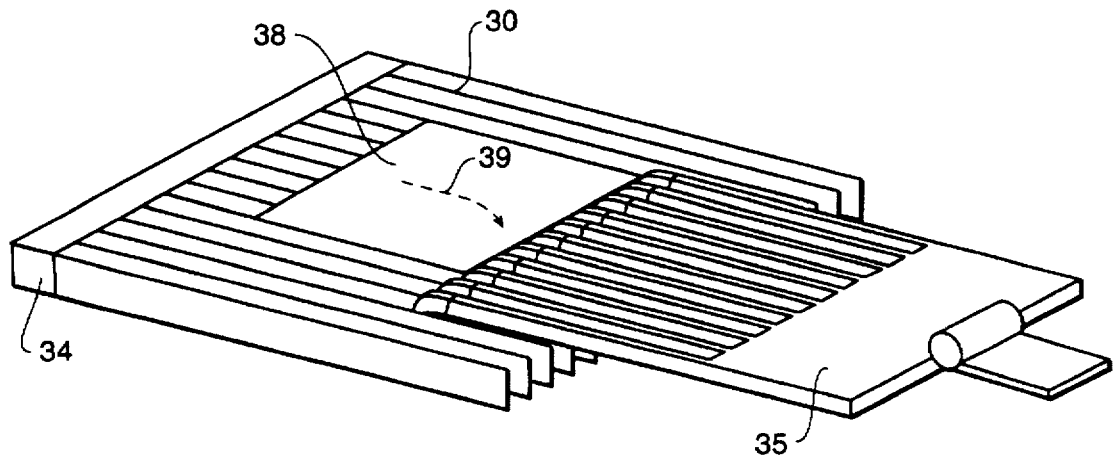
FIGS. 7A and 7B show a first embodiment of a rake included in the cutting device of the present invention being used to pull a wide strip of skin through plural blades.

Cutting device 29 operates to cut wide strips of skin into narrow strips of skin as follows. A wide strip of skin 38 is placed on blades 30 as shown in FIG. 7A. Wide strip of skin 38 is placed top down, meaning that the skin exterior faces downward, towards cutting surface 32. Preferably, wide strip of skin 38 is placed on blades 30 so that hairs growing therefrom extend downward between blades 30 and are substantially parallel to blades 30. As noted, such a placement reduces injuries to hair follicles and facilitates cutting of the strip of skin.

Figure 7B:
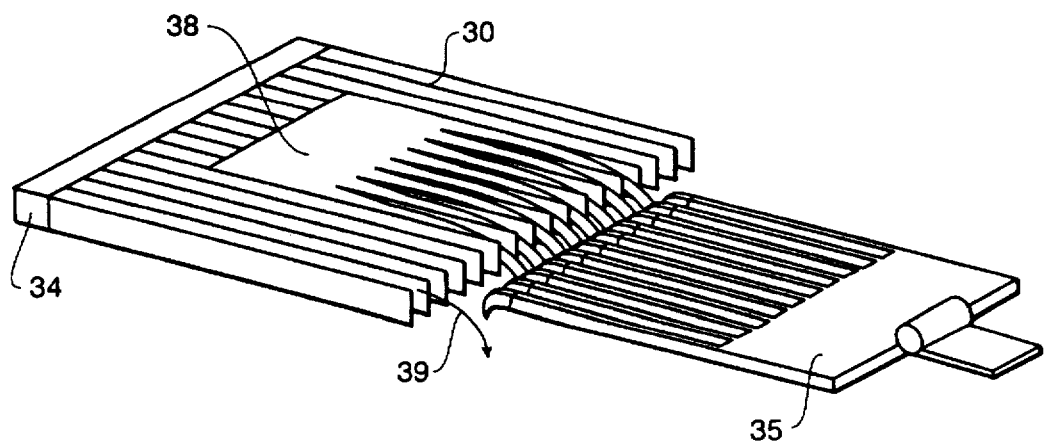

Once wide strip of skin 38 has been placed on blades 30, as described above, rake 35, shown in FIG. 7A, is moved into contact with wide strip of skin 38. Thereafter, rake 35 is pulled in the direction of arrow 39, i.e., along a direction of blades 30 and downward through blades 30, so as to pull wide strip of skin 38 through blades 30. This process is depicted in FIG. 7B, which shows wide strip of skin 38 being cut into plural narrow strips of skin by blades 30. It is noted that rake 35 can also be positioned to grab wide strip of skin 38 from its underside. In any event, the foregoing pulling cuts wide strip of skin 38 into plural narrow strips of skin, each having a width substantially equal to that of a single hair graft. These narrow strips of skin can then be cut into hair grafts.

Rake 58, shown in FIG. 6F, can be used in a similar manner to pull a wide strip of skin through blades 30. Since the foregoing process is identical for rake 35 and rake 58, a detailed description of rake 58 pulling a wide strip of skin through blades 30 is omitted for the sake of brevity.

Figure 8A:
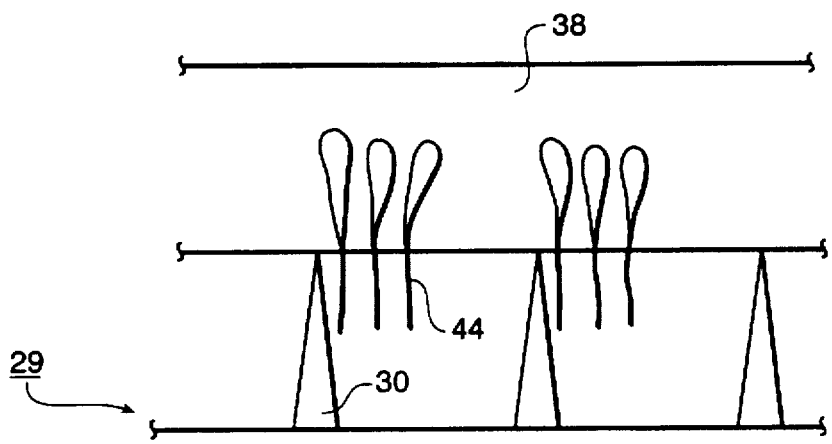
FIGS. 8A, 8B and 8C show close-up views of the cutting device of the present invention being used to cut a single wide strip of skin into plural narrow strips of skin.

The cutting process described above is shown step-by-step in FIGS. 8A to 8C. More specifically, FIG. 8A shows wide strip of skin 38 placed, top down, onto blades 30 such that hairs 44 growing therefrom are substantially parallel to blades 30.

Figure 8B:
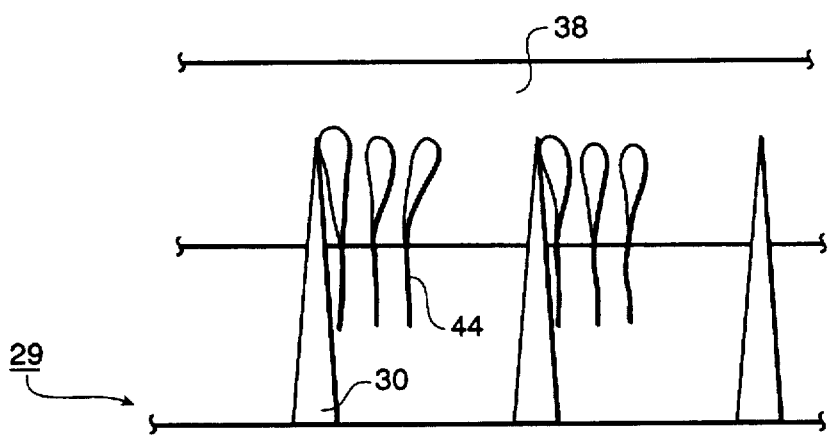

FIG. 8B shows blades 30 beginning to contact the hair follicles of hairs 44. As shown, due to the resistance of the hair follicles for hairs 44, blades 30, rather than cutting through the hair follicles, push those hair follicles aside during cutting.

Figure 8C:
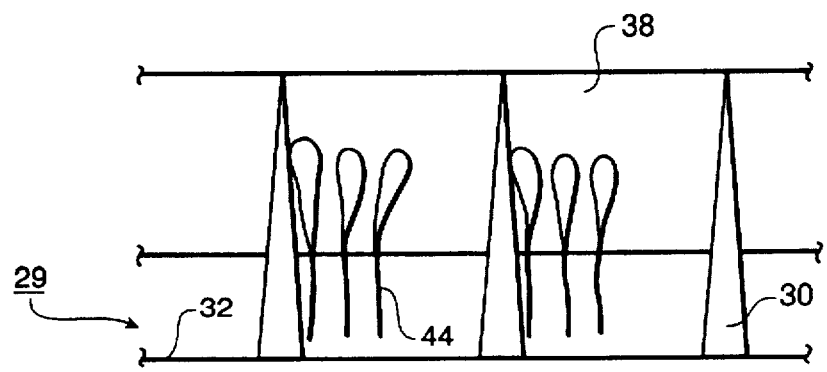

FIG. 8C shows blades 30 having cut past the hair follicles without damaging the hair follicles significantly. By using cutting device 29 in this manner, wide strip of skin 38 can be cut into plural narrow strips of skin without damaging the hair follicles significantly.

Figure 9A:
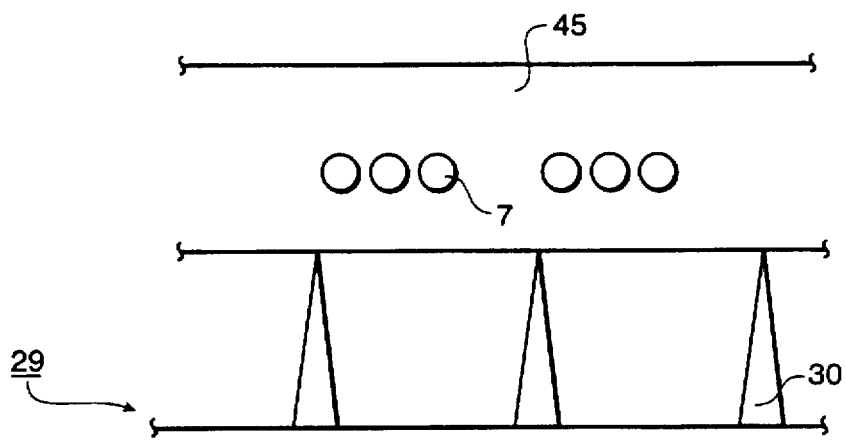
FIGS. 9A, 9B and 9C show close-up views of the cutting device of the present invention being used to cut a narrow strip of skin into hair grafts.
Figure 9B:
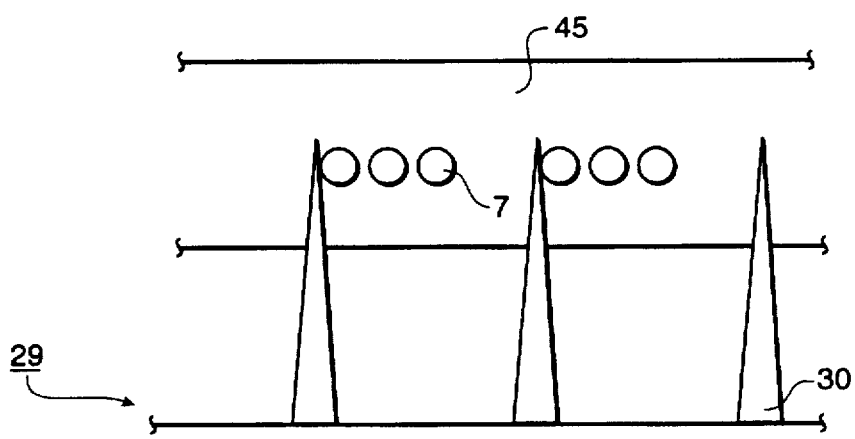
Figure 9C:
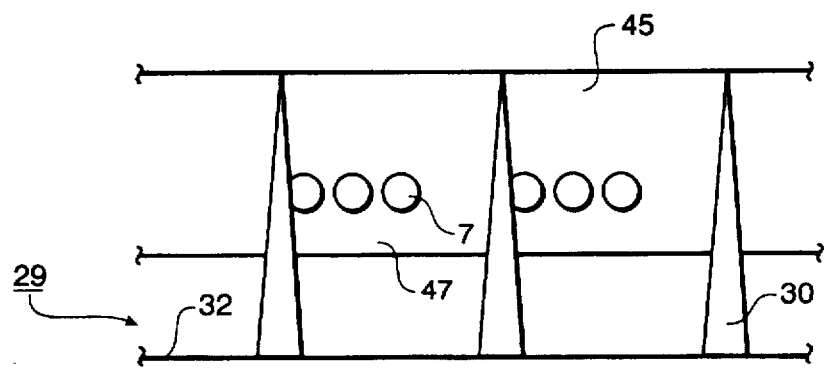

Cutting device 29 operates to cut narrow strips of skin into hair grafts as shown in FIGS. 9A to 9C. More specifically, a narrow strip of skin, such as strip 45 shown in FIG. 6A, is placed sideways on blades 30 in a direction such that hairs growing from strip 45 are substantially parallel to the cutting edges of blades 30. This is shown in detail in FIG. 9A, which depicts strip of skin 45 having hair follicles 7 placed sideways on plural blades 30. It is noted that hair follicles 7 are drawn as circles to indicate that hairs growing from these hair follicles face out of the page.

Once strip 45 is placed on blades 30, downward lateral force in the direction of arrow 46 of FIG. 6A is applied to plate 31. This force causes rotatable members 33 to rotate in the direction of arrows 40 and to move plate 31 into contact with blades 30, thus sandwiching strip 45 between plate 31 and blades 30. Upon application of sufficient force, plate 31 forces strip 45 down onto blades 30, thereby cutting strip 45 into individual hair grafts 47 with protruding hair follicles 7. Thus, FIG. 9B shows blades 30 beginning to cut through strip of skin 45, and FIG. 9C shows blades 30 cut all the way through strip of skin 45 to produce hair grafts 47. As shown, because hair follicles 7 provide greater resistance than the surrounding skin, blades 30 push hair follicles 7 aside, rather than cutting through them.

FIGS. 6D and 6E show a rake, in this case rake 35, being used to remove hair grafts 47, cut via the foregoing process, from in between blades 30. In this regard, FIG. 6D shows rake 35 scooping cut hair grafts from above blades 30, whereas FIG. 6E shows rake 35 in position to lift cut hair grafts from below blades 30. Either method can be used.

During its use, cutting device 29 is cooled and moistened with saline so as to prolong the viability of strips of skin and hair grafts cut therefrom.

It is noted that while cutting device 29 has been described with respect to cutting single strips of skin, cutting device 29 is preferably used to cut plural strips of skin, both wide and narrow, simultaneously, thereby speeding up the entire hair transplantation procedure.

Referring back to FIG. 1, following step S102, the process proceeds to step S103. In step S103 hair grafts 47, shown in FIG. 6D, are sequentially loaded, bottom down, i.e., subcutaneous layer down, into a removable cartridge which connects to an instrument for implanting the hair grafts into recipient region 48 (see FIG. 2) of a patient's scalp. Hair grafts 47 are loaded so as to create an air seal between hair grafts 47 and the cartridge. The cartridge into which hair grafts 47 are loaded and stored is described in detail below.

Cartridge Which Stores Hair Grafts

Figure 10A:
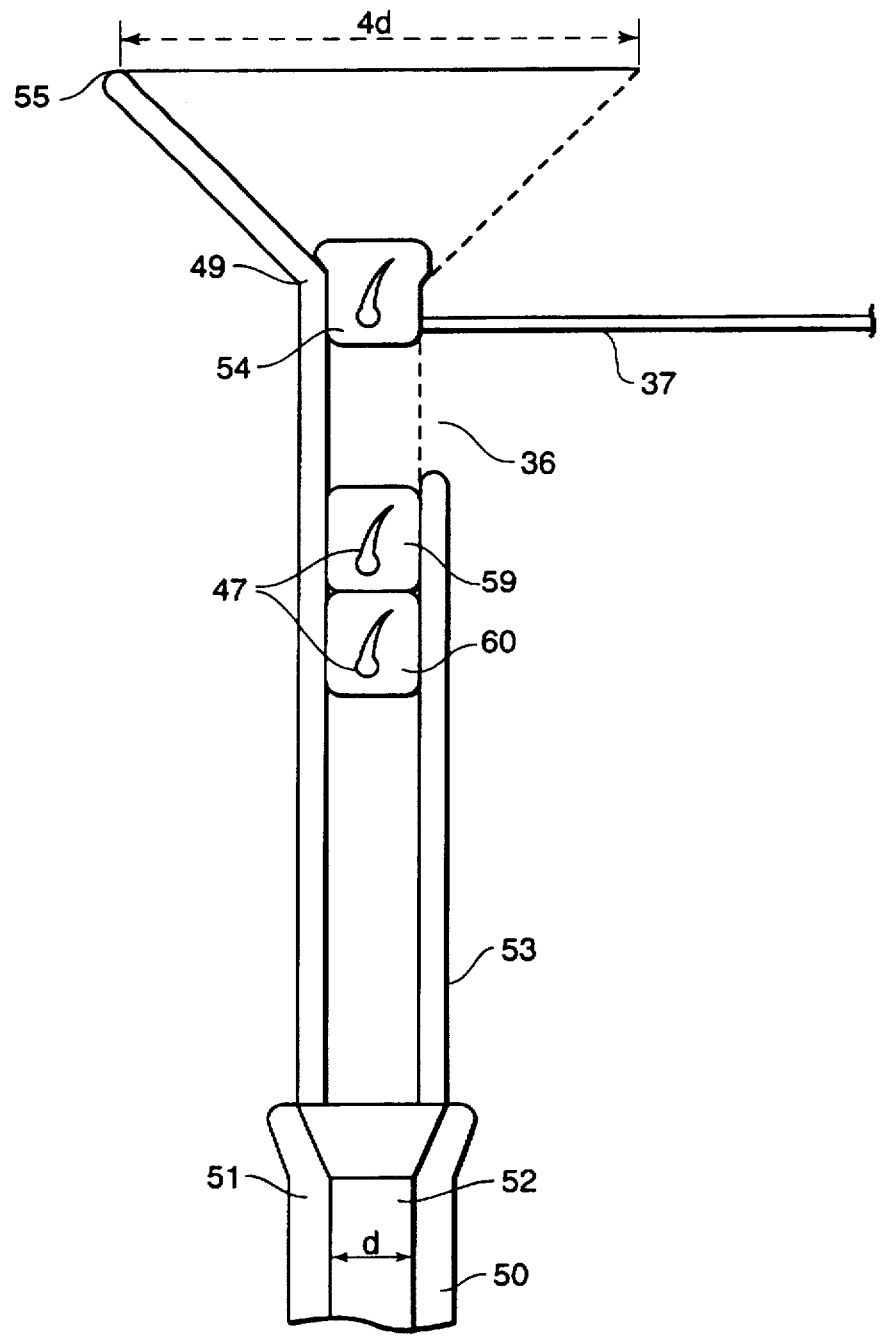
FIGS. 10A and 10B show views of a cartridge for storing hair grafts according to the present invention.
Figure 10B:
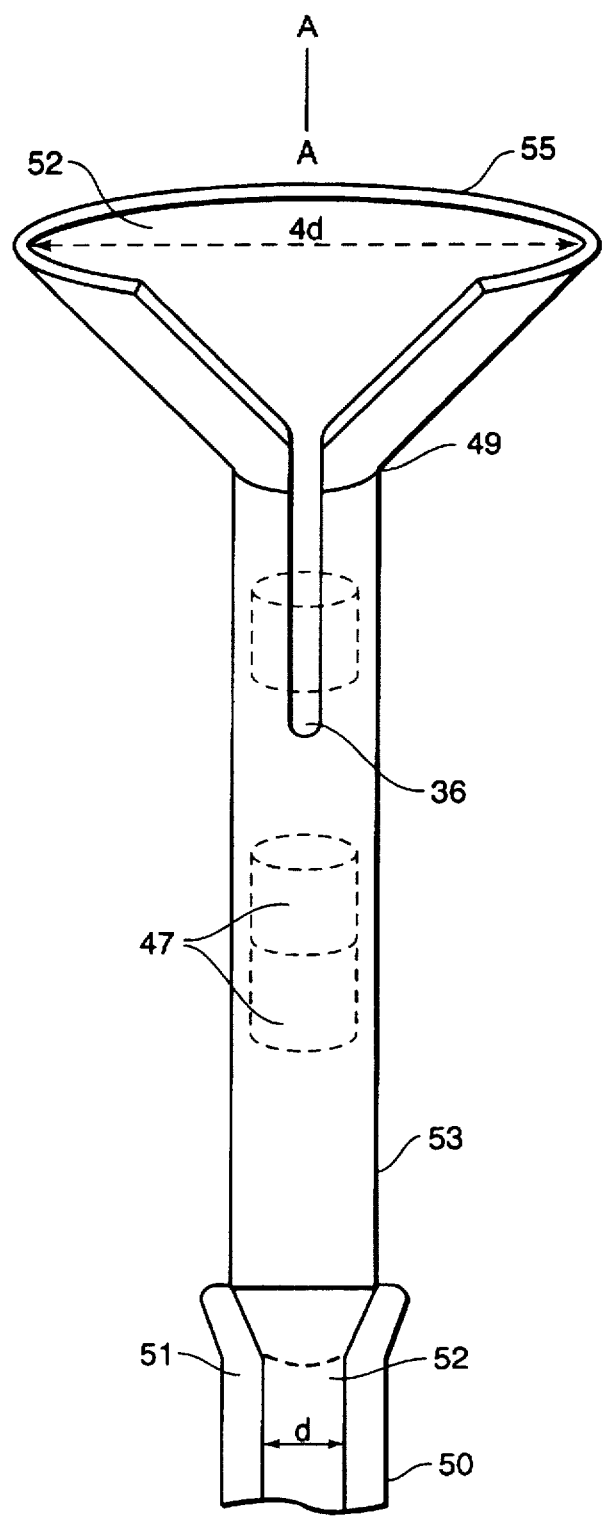
Figure 11:
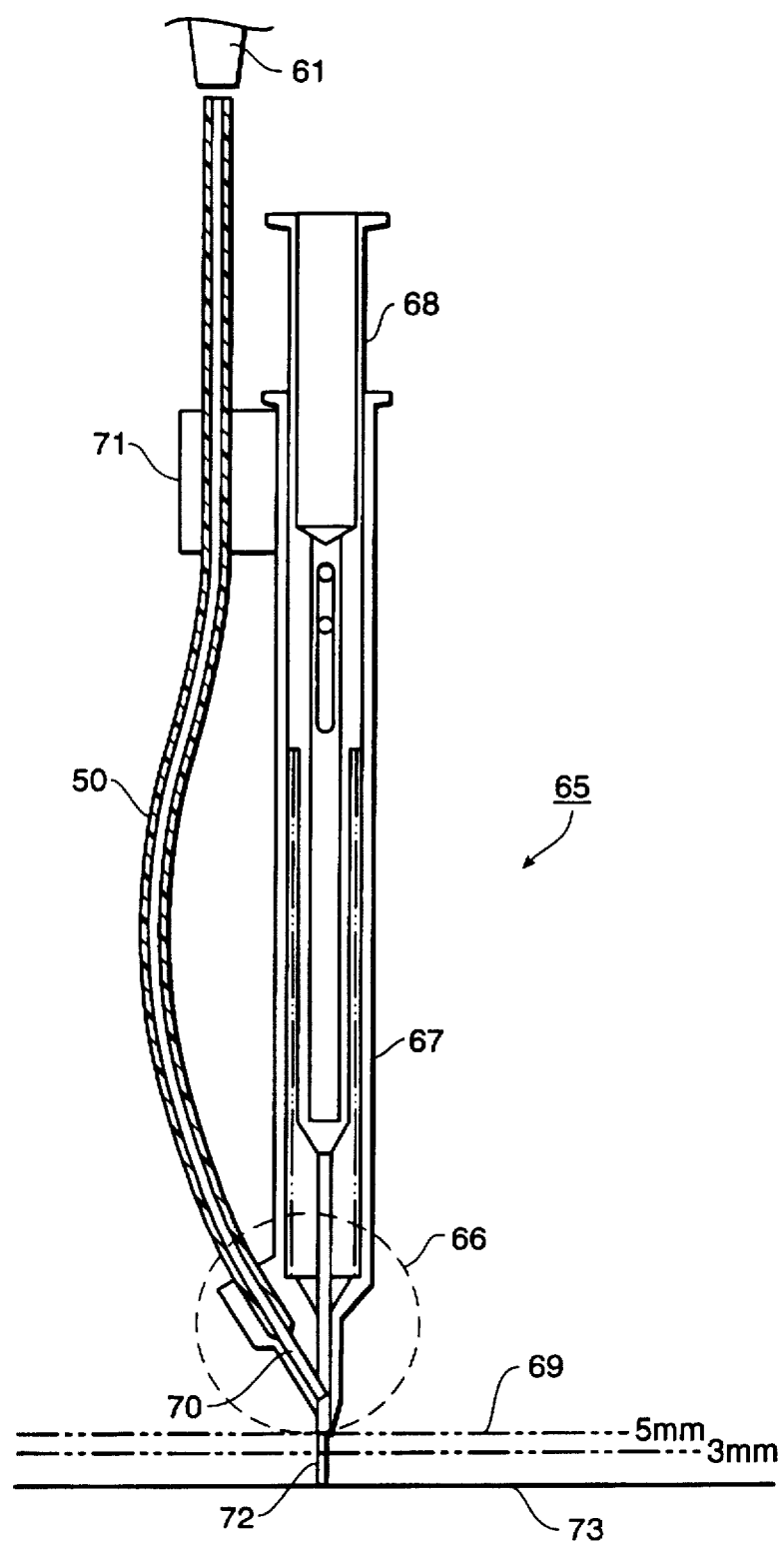
FIG. 11 shows a view of an instrument for implanting hair grafts according to the present invention.

FIG. 11 shows an overall view of cartridge 50 of the present invention. FIG. 10A shows a cross-sectional sideview of cartridge 50 and of neck 53, which attaches to cartridge 50, taken along line A—A of Figure 10B. Cartridge 50 stores plural hair grafts 47 which have been cut by cutting device 29, or otherwise. Each of hair grafts 47 contains N (N≧1) hairs growing therefrom, and is fed to cartridge 50 through neck 53.

Cartridge 50 includes tubular body 51 having continuous throughbore 52. Continuous throughbore 52 has a cross-sectional area sufficient to accommodate a single hair graft. Attached to cartridge 50 is neck 53, which is connected to tubular body 51, through which each of hair grafts 47 is sequentially loaded, bottom down, into tubular body 51. Slot 36 runs along neck 53 to permit contact with a hair graft by an external instrument. The external instrument slides the hair graft along the slot to load the hair graft into the cartridge. Neck 53, preferably, has a funnel shape, such that top portion 55 of neck 53 has a greater radius (i.e., length 2d) than tubular body 51 (i.e., length d/2).

According to the present invention, each individual hair graft, such as hair graft 54 shown in FIG. 10A, is fed through neck 53 into tubular body 51 via needle 37 or the like. In this manner, a hair graft, such as hair graft 54 shown in FIG. 10A, is fed into cartridge 50. Needle 37, inserted into neck 53 via slot 36, grabs onto hair graft 54 and drags hair graft 54 into contact with a next hair graft in cartridge 50. As each hair graft is dragged down, the hair graft forces the next hair graft, and any succeeding hair grafts, down cartridge 50. In this manner, hair grafts are loaded into cartridge 50.

In this regard, in cartridge 50, the cross-sectional area of continuous throughbore 52 should be sized so as to fit hair graft 54, yet small enough to create an air seal between each hair graft, such as hair graft 54, and tubular body 51. As described below, this air seal is used to feed each hair graft to an implant-ready position as each preceding hair graft is implanted from cartridge 50 into a patient's scalp.

In addition, cartridge 50 can include pressurizing mechanism 61, shown in FIG. 11, which supplies pressure to cartridge 50 in order to assist movement of hair grafts down tubular body 51. Pressurizing mechanism 61 can be an air pump, or the like, which fits inside of or over tubular body 51, and which creates an air seal between itself and tubular body 51 in order to supply air pressure down cartridge 50. By supplying pressure from the top of cartridge 50, pressurizing mechanism 61 decreases the chances that a hair graft will get stuck in tubular body 51 and that a hair graft will not feed from the cartridge.

To facilitate movement of the hair grafts down continuous throughbore 52, surfaces of tubular body 51 which make up continuous throughbore 52, and surfaces inside of neck 53, should be substantially smooth and preferably made of a material such as glass, plastic or stainless steel, which is slippery relative to the fatty composition of the hair graft. Lubricants other than saline solution are generally not required during loading of the hair grafts into cartridge 50, since fat from around hair follicles on the hair grafts acts as a natural lubricant.

Figures 12A, 12B, 12C:
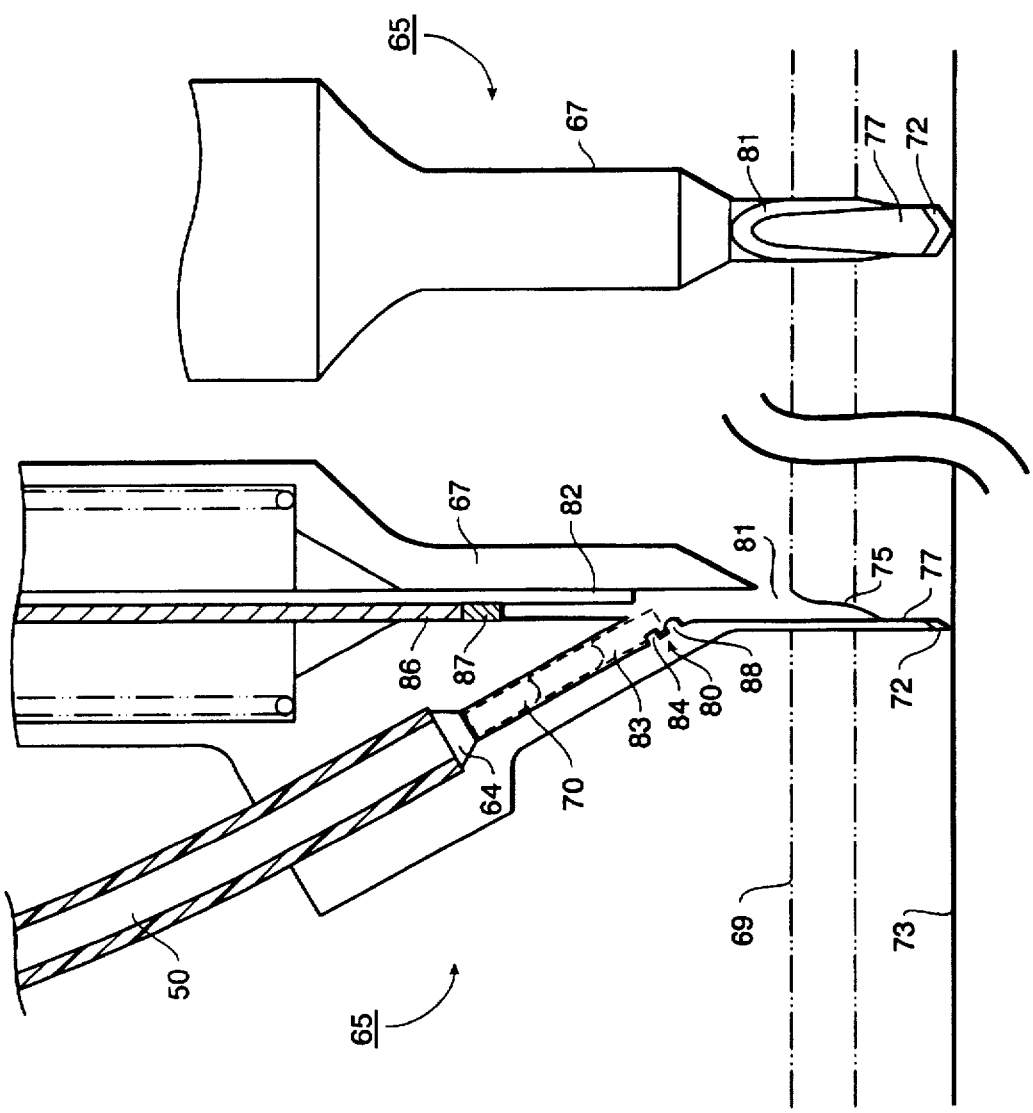
FIGS. 12A, 12B and 12C show close-up views of the instrument of FIG. 11.

Cartridge 50 also includes connecting end 64, located at an opposite end of tubular body 51 than neck 53, which connects cartridge 50 to an instrument for implanting a hair graft into a patient's scalp (see FIG. 12A). As shown in FIG. 12A, connecting end 64 fits inside of feeding tube 70, from which hair grafts are fed for implantation. By virtue of this configuration, cartridge 50 can be easily removed from the instrument and replaced with another pre-loaded cartridge. As a result, the cartridge reduces the time it takes to re-supply hair grafts to the instrument.

In preferred embodiments of the invention, cartridge 50, including neck 53, is made from a flexible material, such as surgical tubing, and neck 53 is removable. Neck 53's removability is shown by FIG. 11, which depicts cartridge 50 without neck 53.

Following loading of cartridge 50, it is moistened and cooled in a misting unit (not shown), prior to implanting hair grafts stored in cartridge 50. This is done in order to maintain viability of the hair grafts. If maintained properly in cartridge 50, the hair grafts can remain viable longer than 72 hours after harvesting.

Referring back to FIG. 1, once hair grafts 47, which have been cut by the foregoing processes, are loaded into cartridge 50, processing proceeds to step S104. In step S104, hair grafts from cartridge 50 are implanted into recipient region 48 of the patient's scalp (see FIG. 2), one at a time.

Implanting of hair grafts can be accomplished using the hair transplantation device described in Applicant's co-pending U.S. patent application Ser. No. 08/444,923. Alternatively, implanting can be accomplished using the instrument for implanting hair grafts mentioned above. This is done by feeding a hair graft to a predetermined feed position in the instrument via air suction created by an air seal between each loaded hair graft and cartridge 50, making an incision at a point in recipient region 48 of the patient's scalp at which the hair graft is to be implanted using a cutting device, such as a microsurgical blade or a knife, on the instrument, and sliding the hair graft into the incision using an implanting member in the instrument. This process is described in more detail below, preceded by a detailed description of the foregoing instrument.

Instrument For Implanting Hair Grafts

The foregoing instrument for implanting hair grafts into a patient's scalp implants hair grafts fed, bottom down, via air suction from a cartridge, such as cartridge 50 described above, which sequentially stores air-sealed hair grafts. The instrument includes an elongate housing adapted to be manipulated by a surgeon during implantation of the hair grafts, and a cutting device, such as a microsurgical blade or a knife, affixed to an end of the elongate housing for making an incision into the patient's scalp, into which a hair graft is to be implanted. Also included in the instrument is a feeding tube which connects the instrument to the cartridge, which stores the hair grafts, and which feeds a hair graft from the cartridge to a predetermined feed position. The feeding tube includes a vent positioned at the predetermined feed position, such that when the hair graft is moved past the predetermined feed position, air from the vent breaks an air seal between the hair graft and a next-sequential hair graft in the cartridge. An implanting member (1) moves downward through the elongate housing, (2) contacts the hair graft at the predetermined feed position, and (3) slides the hair graft into the incision made in the patient's scalp by the cutting device through an opening formed between the cutting device and the elongate housing. A plunger, disposed within the elongate housing, actuates the implanting member.

In preferred embodiments, as described in more detail below, the instrument includes a holding member which (1) moves downward through the elongate housing in a substantially same direction as the implanting member, (2) contacts the hair graft contacted by the implanting member, and (3) remains in contact with the hair graft during withdrawal of a portion of the instrument from the incision. The holding member is also actuated by the plunger. It is noted that the instrument described herein for implanting hair grafts need not include such a holding member. However, for the sake of brevity, an embodiment of the invention which includes the holding member will be described.

An overall view of a representative embodiment of instrument 65, which is an instrument for implanting hair grafts according to the present invention, is shown in FIG. 11. A cross-sectional side view and front views of circular-region 66 of instrument 65 are shown in FIGS. 12A to 12C.

Referring to FIG. 11, that figure shows elongate housing 67 and plunger 68, which actuates both the implanting and holding members described above when instrument 65 is inserted into scalp 69 of a patient.

FIG. 11 also shows cartridge 50 installed in instrument 65. Specifically, as shown, cartridge 50 is installed onto feeding tube 70 of instrument 65. As described in more detail below, this configuration permits feeding of hair grafts from cartridge 50 to instrument 65 via air suction.

Figure 13:
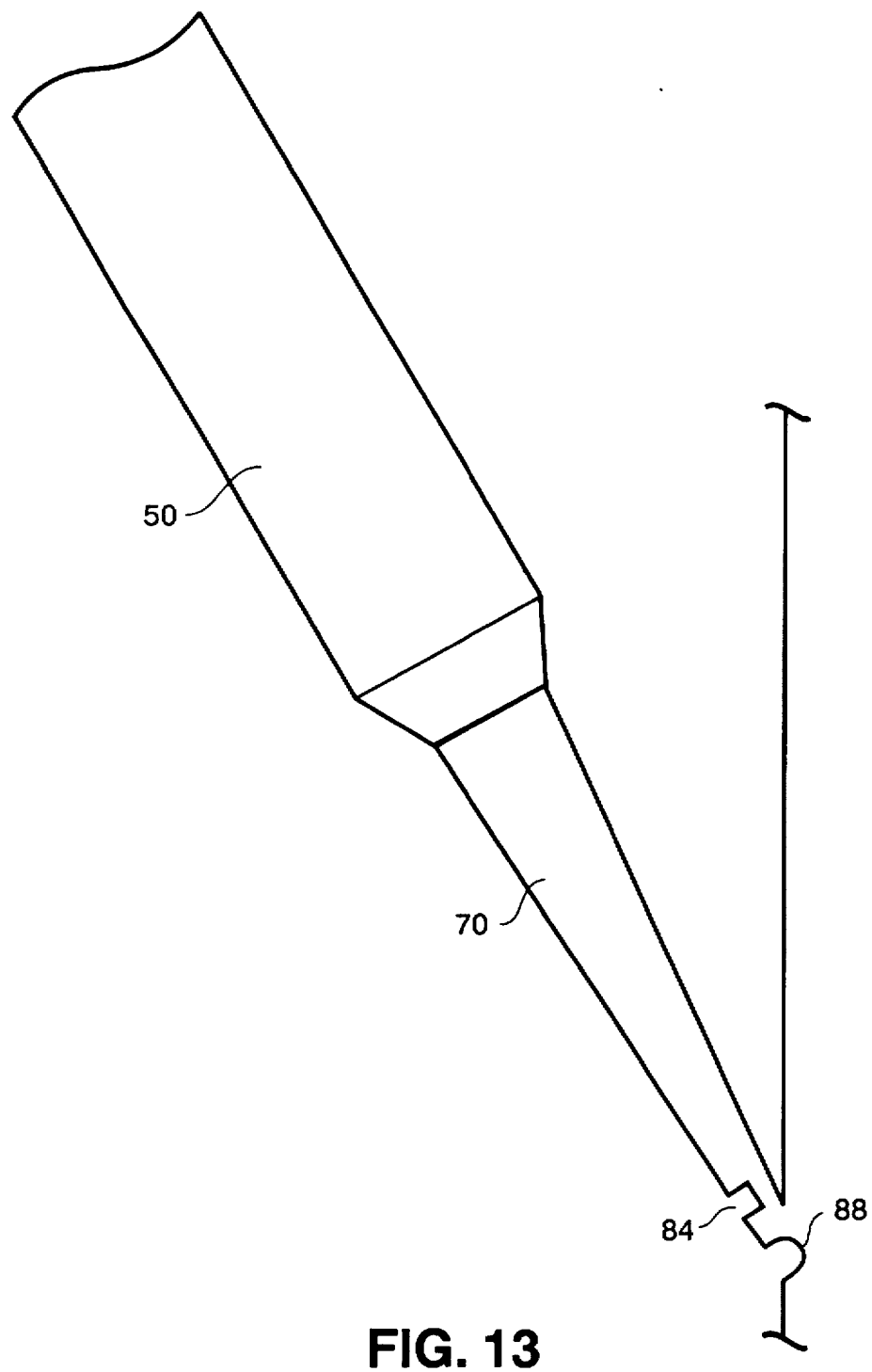
FIG. 13 shows a close-up view of a gradually-narrowing feeding tube used in the instrument of FIG. 11.

In preferred embodiments, feeding tube 70 includes a mechanical stop at the feed position, such as stop 88, shown in FIG. 12A, so as to reduce the chances that pressure applied from the top of cartridge 50 will cause hair grafts from feeding tube 70 to feed prematurely. Examples of such a mechanical stop include a nub or a mechanical resistor. This same function can be achieved by gradually narrowing feeding tube 70 as feeding tube 70 approaches the predetermined feed position. An example of this configuration is shown in FIG. 13.

Holder 71, shown in FIG. 11, holds cartridge 50 to instrument 65. Holder 71 can either be an attachment to elongate housing 67 or an integrally-formed part thereof.

A cutting device, such as microsurgical blade 72, also shown in FIG. 11, penetrates scalp 69 of the patient to reach patient's skull 73 in order to create an incision into which a hair graft is implanted.

As noted, the foregoing is shown close-up in FIGS. 12A and 12B, which show microsurgical blade 72 penetrating roughly 5 millimeters into scalp 69 to reach skull 73. Such penetration can, of course, be varied, depending upon the thickness of a patient's scalp, and other pertinent factors. This penetration creates incision 75.

Microsurgical blade 72, as seen from the front view depicted in FIG. 12B, typically has a V shape, and has a smooth, substantially planar surface 77, as seen from the side view depicted in FIG. 12A.

FIG. 12A shows cartridge 50 connected to feeding tube 70 via connecting end 64. As noted above, cartridge 50 contains air-sealed hair grafts such as hair grafts 54, 59 and 60 (shown in FIG. 10A), which feed down to instrument 65 by air suction and, in some embodiments, air pressure, from cartridge 50, through feeding tube 70, to predetermined feed position 80.

In preferred embodiments of the instrument, feeding tube 70 is angled with respect to the feeding direction. This is shown in the front view of feeding tube 70 depicted in FIG. 12C. Such a configuration facilitates feeding of hair grafts to predetermined feed position 80 and further reduces injury to those hair grafts during feeding.

As also shown in FIGS. 12A and 12B, instrument 65 includes opening 81 between planar surface 77 of microsurgical blade 72 and elongate housing 67. Hair grafts are implanted from feed position 80, through opening 81, via implanting member 82, also shown in FIG. 12A.

Instrument 65 also includes vent 84. Vent 84 is positioned at predetermined feed position 80. Vent 84 is dimensioned so as to break the air seal between hair graft 83, shown at feed position 80, and a next-sequentially-stored hair graft in cartridge 50 at a point where the next-sequentially-stored hair graft from cartridge 50 reaches feed position 80.

More specifically, as noted above, hair grafts are fed from cartridge 50 via air suction by withdrawing a hair graft from the feeding tube for implantation. As described in more detail below, implanting member 82, shown in FIG. 12A, contacts hair graft 83 at predetermined feed position 80, and slides hair graft 83 through opening 81 into incision 75. As hair graft 83 is implanted, succeeding hair grafts in cartridge 50 are drawn down toward feed position 80 by air suction. As noted, in order to ensure that a next-sequentially-stored hair graft is not fed too far, instrument 65 includes vent 84 (and stop 88), so that the air seal between hair graft 83 and the next-sequentially-stored hair graft in cartridge 50 is broken at the point where the next-sequentially-stored hair graft reaches predetermined feed position 80.

Implanting member 82, as noted above, moves downward through elongate housing 67 to contact hair graft 83 at feed position 80. Once in contact with hair graft 83, implanting member 82 slides hair graft 83 down along planar surface 77 of microsurgical blade 72 into incision 75 in scalp 69. Preferably, implanting member 82 has a length which is sufficient to penetrate an entire depth of scalp 69, in order to ensure proper implantation of the hair grafts. It is, however, noted that implanting member 82 need not penetrate the entire scalp in order to implement the present invention.

As noted above, the instrument described herein need not include a holding member. With respect to embodiments of the instrument that do not include the holding member, suffice it to say that implanting member 82, shown in FIG. 12A, can be sized to take up the space in elongate housing 67 occupied by holding member 86, and that portions of elongate housing 67 can be used to perform the function of the holding member. In such a case, implanting can still be performed as described above. Preferred embodiments of the invention, however, include holding member 86, the structure and function of which are described in detail as follows.

Holding member 86, which moves downward through elongate housing 67 in substantially the same direction as implanting member 82, contacts hair graft 83 at a later point than implanting member 82. This is because, as shown in FIG. 12A, holding member 86 is positioned further upstream in elongate housing 67 than implanting member 82. This effect can be achieved by making holding member 86 shorter than implanting member 82. Holding member 86 contacts hair graft 83 to hold hair graft 83 in place once hair graft 83 has been implanted into incision 75. In this regard, since holding member 86 is merely used to hold an implanted hair graft in place in the incision in the scalp, holding member should not substantially penetrate the hair graft.

In preferred embodiments of the instrument, holding member 86 has a tip, such as tip 87 shown in FIG. 12A, made of an expandable material, such as sponge or its substantial equivalent. Tip 87 should have a size and shape which permits compression inside of elongate housing 67, and expansion outside of elongate housing 67, i.e., when holding a hair graft in place. Tip 87 provides a cushion which reduces injuries to an implanted hair graft which can be caused by holding member 86. When expanded, tip 87 should have a shape which is sufficient to surround implanting member 82 during withdrawal of implanting member 82 from incision 75, so as to provide even further protection for the implanted hair graft.

In preferred embodiments of the instrument, implanting member 82 and holding member 86 move independently of each other. This is of particular relevance during withdrawal of implanting member 82 from incision 75. That is, in preferred embodiments, implanting member 82 is withdrawn from incision 75 while holding member 86 remains in contact with an implanted hair graft. Withdrawal of implanting member 82 can be triggered, for example, by a spring-loaded latch mounted inside of elongate housing 67 which causes implanting member 82 to withdraw once implanting member 82 has been extended a predetermined distance. As a result of this feature, withdrawal of implanting member 82 can be performed without causing the implanted hair graft to be dislodged.

In the present instrument, elongate housing 67 can also be formed to move upward as plunger 68 is depressed. This feature can be used in a case where implanting member 82 is not the first device withdrawn from incision 75, or in a case where implanting member 82 and holding member 86 are not independently movable. In addition, this feature can be combined with the latch described above to reduce dislodging of implanted hair grafts even further. More specifically, in such a case, holding member 86 remains in contact with an implanted hair graft while implanting member 82 is withdrawn from incision 75, and while at least a portion of microsurgical blade 72 is also withdrawn from incision 75.

As noted above, in preferred embodiments of the instrument, plunger 68, which is shown in FIG. 11, is used to actuate both holding me member 82 and holding member 86. Thus, upon application of a predetermined force to plunger 68, movement downward of both implanting member 82 and holding member 86 is commenced inside of elongate housing 67.

FIG. 2 shows instrument 65 being used to implant hair grafts into recipient region 48 of a patient's scalp during a hair transplantation procedure.

Figure 14C:
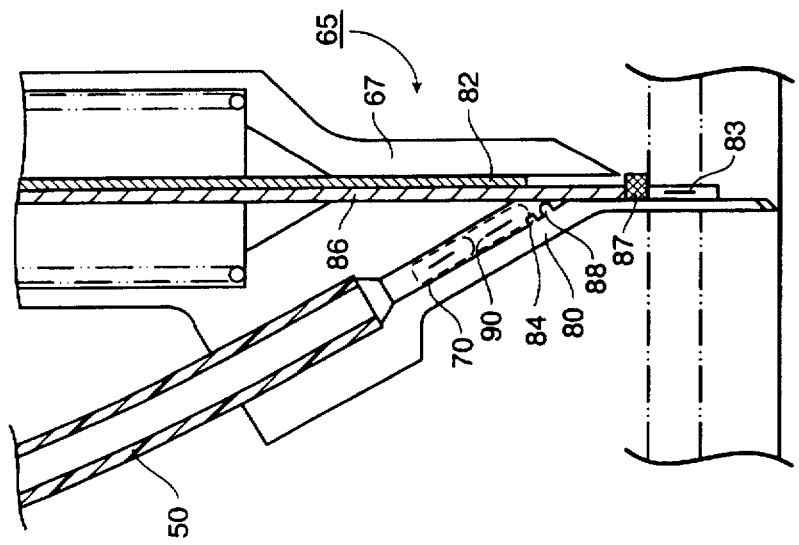
FIGS. 14A, 14B and 14C show the instrument of FIG. 11 during use at various stages of the hair transplantation procedure of the present invention.
Figure 14B:
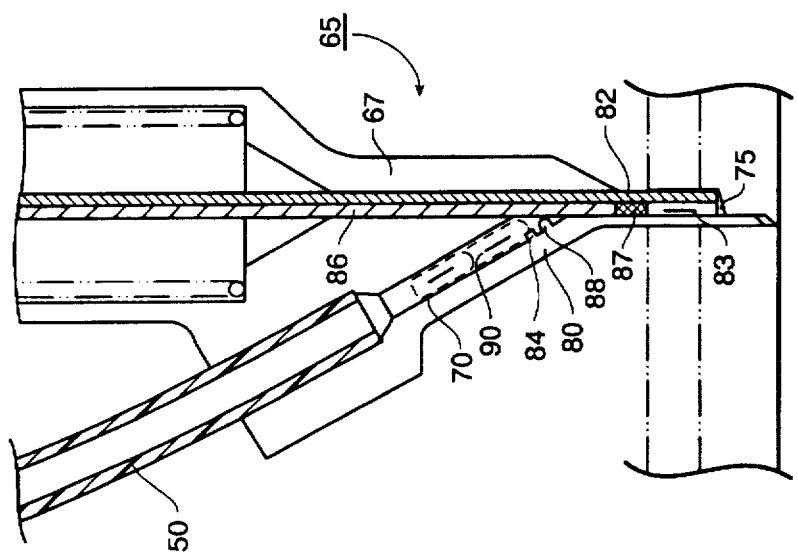
Figure 14A:
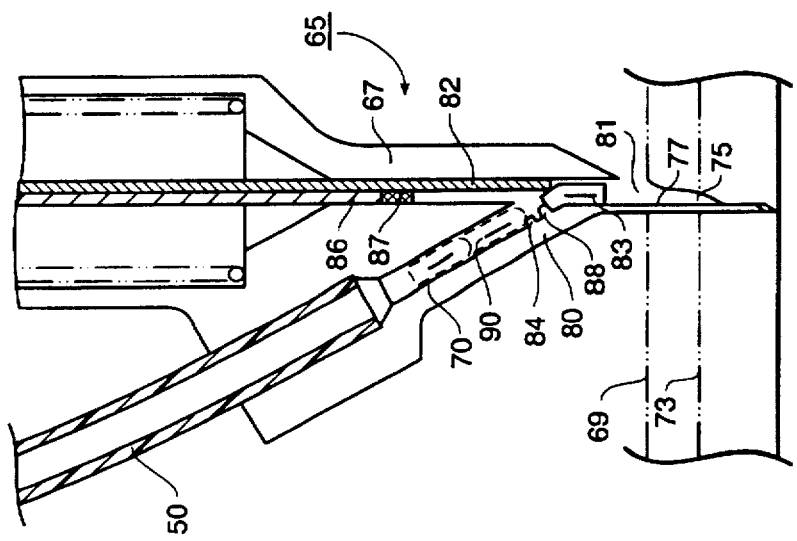
Figure 15:
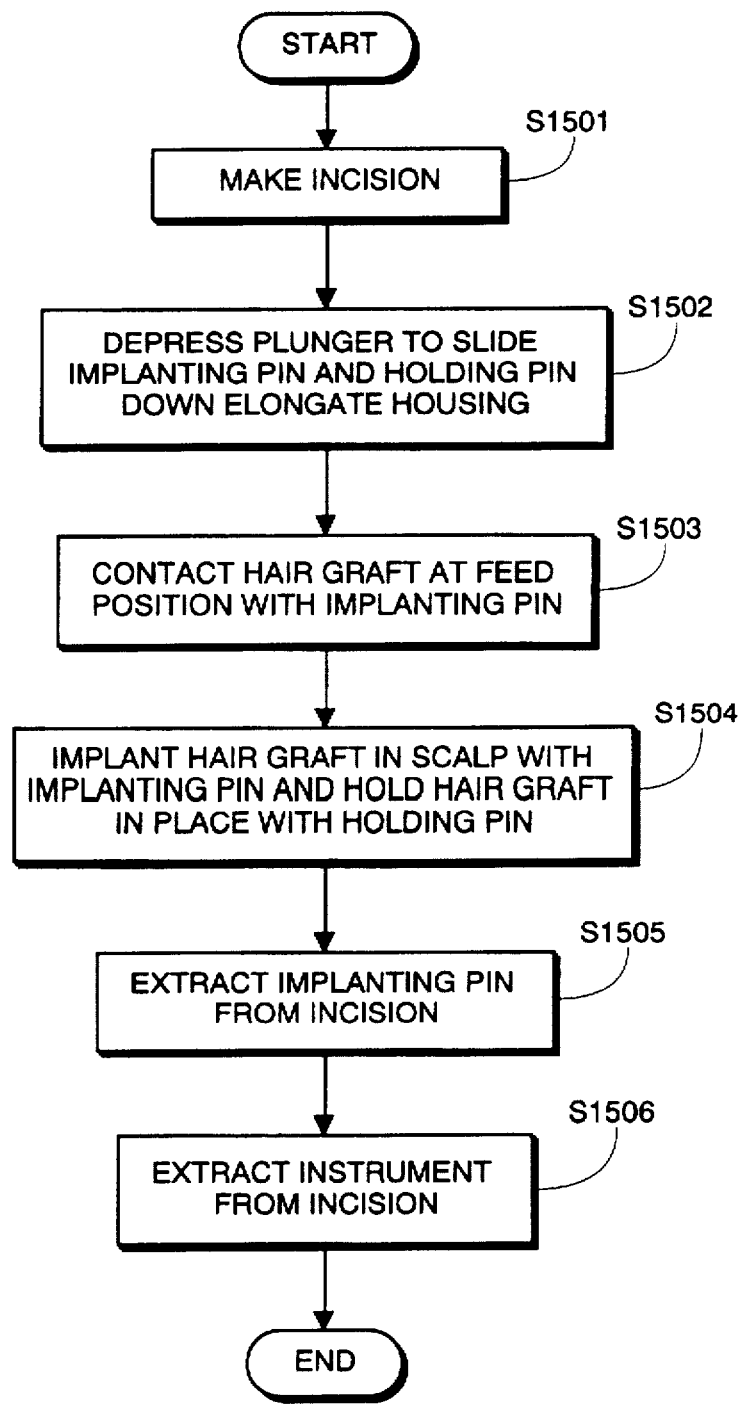
FIG. 15 is a flow diagram showing a procedure for implanting hair grafts using the instrument of FIG. 11.

FIGS. 14A to 14C show instrument 65 at various stages during implanting hair graft 83; and FIG. 15 shows process steps for implanting hair graft 83 using instrument 65. For illustration's sake, instrument 65 comprises the embodiment of the instrument in which an implanting member is withdrawn from an incision while a holding member remains in contact with a hair graft which has been implanted in the incision.

In step S1501, a surgeon makes incision 75 in scalp 69 using microsurgical blade 72 of instrument 65, as shown in FIG. 14A. Next, in step S1502, the surgeon depresses plunger 68 (see FIG. 11) to begin implanting hair graft 83 in incision 75. This causes implanting member 82 and holding member 86 to slide downwardly inside of elongate housing 67 toward incision 75. In step S1503, implanting member 82 contacts hair graft 83 at feed position 80, as shown in FIG. 14A. Thereafter, implanting member 82 slides hair graft 83 over stop 88 and down planar surface 77 of microsurgical blade 72 towards incision 75. It should be noted that during this time next-sequentially-stored hair graft 90 is fed to feed position 80 by air suction.

During sliding of hair graft 83 out of feeding tube 70, hair graft 83 contacts open air via vent 84. This contact breaks the air seal between hair graft 83 and next-sequentially-stored hair graft 90. As noted above, breaking of the air seal is preferably done at a point where next-sequentially-stored hair graft 90 reaches feed position 80. As a result of this, and of stop 88, next-sequentially-stored hair graft 90 stops feeding down feeding tube 70.

Next, in step S1504, hair graft 83 is implanted in incision 75 by implanting member 82, and is contacted by holding member 86, as shown in FIG. 14B. It should be noted that although the present embodiment describes holding member 86 contacting hair graft 83 when hair graft 83 is implanted in incision 75, holding member 86 can come into contact with hair graft 83 at any point in the process. In addition, as shown in FIG. 14B, holding member 86 does not substantially penetrate hair graft 83. Instead, holding member 83 merely holds hair graft 83 in place in incision 75.

FIG. 14C depicts step S1505. Specifically, FIG. 14C depicts withdrawal of implanting member 82 from incision 75, while holding member 86 remains in contact with implanted hair graft 83. As indicated above, withdrawal of implanting member 82 can be triggered by a spring-loaded latch or its substantial equivalent. Following withdrawal of implanting member 82, in step S1506, instrument 65 is withdrawn from incision 75, leaving a transplanted hair graft to grow in incision 75. Thereafter, the process of FIGS. 14A to 14C is repeated throughout a recipient region of the patient's scalp.

It is noted that the process of FIG. 15 can be performed by using plural instruments, such as instrument 65, simultaneously on a single patient.

The present invention has been described with respect to particular illustrative embodiments. It is to be understood that the invention is not limited to the above-described embodiments and modifications thereto, and that various changes and modifications may be made by those of ordinary skill in the art without departing from the spirit and scope of the appended claims.

What is claimed is:

1. An instrument for implanting hair grafts into a patient's scalp, said instrument comprising:

an elongate housing adapted to be manipulated by a surgeon during implantation of the hair grafts, the elongate housing having a bore extending at least part way into the elongate housing from an implanting end of the elongate housing;

a cutting device affixed to the implanting end of said elongate housing for making an incision into the patient's scalp, into which a hair graft is to be implanted;

a feeding station, including a passageway through which a hair graft is fed to a predetermined feed position adjacent to the bore in the elongate housing, the passageway including cartridge receiving means for receiving a cartridge which stores hair grafts sequentially, one behind another, such that an air seal exists between each hair graft and the cartridge, the hair grafts being fed from the cartridge, through the passageway, subcutaneous-end first;

an implanting member which is adapted (1) to move downward through the bore in said elongate housing, (2) to contact the hair graft at the predetermined feed position, and (3) to slide the hair graft into the incision made in the patient's scalp by said cutting device through an opening formed between said cutting device and said elongate housing, wherein as the implanting member slides the hair graft into the incision, air suction draws a next sequential air-sealed hair graft from the cartridge, through the passageway, to the predetermined feed position; and a plunger which is adapted to actuate said implanting member.

2. An instrument according to claim 1, further comprising a holding member which is adapted (1) to move downward through the bore in said elongate housing in a substantially same direction as said implanting member, (2) to contact the hair graft contacted by said implanting member, and (3) to remain in contact with the hair graft during withdrawal of a portion of said instrument from the incision;

wherein said plunger also activates said holding member.

3. An instrument according to claim 2, wherein said implanting member and said holding member move independently; and wherein said holding member remains in contact with the hair graft implanted in the incision during withdrawal of said implanting member from the incision.

4. An instrument according to claim 3, further comprising a latch connected to said implanting member which triggers withdrawal of said implanting member from the incision while said holding member remains in contact with the hair graft in the incision.

5. An instrument according to claim 3, wherein said holding member extends outside of said elongate housing when in contact with the hair graft; and wherein said holding member includes an expandable tip at an area which contacts the hair graft, which expands when said holding member is outside of said elongate housing.

6. An instrument according to claim 5, wherein the expandable tip is made of a spongy material; and wherein the expandable tip has a size and a shape which are sufficient to permit the expandable tip to surround said implanting member while said implanting member is being withdrawn from the incision.

7. An instrument according to claim 2, wherein said implanting member is extended to penetrate an entire depth of the patient's scalp; and wherein said holding member is extended to contact the patient's scalp when said implanting member is in the incision created by said cutting device.

8. An instrument according to claim 1, wherein said elongate housing is movable, such that said elongate housing moves upward away from the patient's scalp while said implanting member is in the incision.

9. An instrument according to claim 1, wherein a surface of said cutting device which faces said implanting member is substantially planar; and wherein said implanting member slides the hair graft into the incision along the substantially planar surface of said cutting device.

10. An instrument according to claim 3, wherein said passageway is more narrow at the predetermined feed position than at the cartridge receiving means.

11. An instrument according to claim 1, further comprising a mechanical stop located at the predetermined feed position.

12. An instrument according to claim 1, wherein the passageway includes a vent positioned at the predetermined feed position, such that when the hair graft moves past the predetermined feed position, air from the vent breaks an air seal between the hair graft and a next-sequential hair graft fed from the cartridge.

13. An instrument for implanting hair grafts into a patient's scalp, the instrument comprising:

an elongate housing adapted to be manipulated by a surgeon during implantation of the hair grafts, the elongate housing having a bore extending at least part way into the elongate housing from an implanting end of the elongate housing;

a cutting device affixed to the implanting end of the elongate housing for making an incision into the patient's scalp, into which a hair graft is to be implanted;

a feeding station including a passageway through which a hair graft is fed to a predetermined feed position adjacent to the bore in the elongate housing, the passageway including cartridge receiving means for receiving a cartridge which stores the hair grafts, the hair grafts being fed subcutaneous-end first from the cartridge through the passageway;

an implanting member which is adapted (b 1) to move downward through the bore in the elongate housing, (2) to contact the hair graft at the predetermined feed position, (3) to slide alongside at least part of the hair graft, and (4) while alongside the hair graft, to slide the hair graft into the incision made in the patient's scalp by the cutting device through an opening formed between the cutting device and the elongate housing; and a plunger which is adapted to actuate the implanting member.

14. An instrument according to claim 13, further comprising a cartridge which connects to the cartridge receiving means and which stores the hair grafts sequentially, one behind another, such that an air seal exists between each hair graft and the cartridge;

wherein as the implanting member slides the hair graft into the incision, air suction draws a next sequential air-sealed hair graft from the cartridge, through the passageway, to the predetermined feed position.

15. An instrument according to claim 14, wherein the passageway includes a vent positioned at the predetermined feed position, such that when the hair graft moves past the predetermined feed position, air from the vent breaks an air seal between the hair graft and a next-sequential air-sealed hair graft from the cartridge.

16. An instrument according to claim 13, wherein the passageway is more narrow at the predetermined feed position than at the cartridge receiving means.

* * * * *

UNITED STATES PATENT AND TRADEMARK OFFICE
CERTIFICATE OF CORRECTION

PATENT NO. : 5,782,851
DATED : July 21, 1998
INVENTOR : WILLIAM R. RASSMAN

It is certified that error appears in the above-identified patent and that said Letters Patent is hereby corrected as shown below:

COLUMN 1

Line 45, delete "to" (second occurence).

COLUMN 4

Line 18, change "portion" to --portion of--.

COLUMN 6

Line 1, delete "as".

Line 22, change "embodiments" to --embodiments of--.

COLUMN 20

Line 4, change "claim 3," to --claim 1,--.

Line 36, change "(b 1)" to --(1)--.

Signed and Sealed this

First Day of June, 1999

Attest:

Q. TODD DICKINSON

*Attesting Officer*  *Acting Commissioner of Patents and Trademarks*